US006979675B2

(12) United States Patent
Tidmarsh

(10) Patent No.: US 6,979,675 B2
(45) Date of Patent: Dec. 27, 2005

(54) TREATMENT OF CANCER WITH 2-DEOXYGLUCOSE

(75) Inventor: George Tidmarsh, Portola Valley, CA (US)

(73) Assignee: Threshold Pharmaceuticals, Inc., Redwood City, CA (US)

(*) Notice: Subject to any disclaimer, the term of this patent is extended or adjusted under 35 U.S.C. 154(b) by 0 days.

(21) Appl. No.: 10/754,239

(22) Filed: Jan. 9, 2004

(65) Prior Publication Data

US 2004/0167079 A1    Aug. 26, 2004

Related U.S. Application Data

(60) Provisional application No. 60/496,163, filed on Aug. 18, 2003, provisional application No. 60/460,012, filed on Apr. 2, 2003, provisional application No. 60/458,846, filed on Mar. 28, 2003, provisional application No. 60/458,665, filed on Mar. 28, 2003, provisional application No. 60/439,266, filed on Jan. 10, 2003.

(51) Int. Cl.$^7$ .................. A01N 43/04; A61K 31/70

(52) U.S. Cl. ................... 514/23; 514/24; 514/25

(58) Field of Search ................... 514/23, 24, 25

(56) References Cited

U.S. PATENT DOCUMENTS

| 4,315,001 | A   |   | 2/1982  | Blough            |          |
|-----------|-----|---|---------|-------------------|----------|
| 5,185,325 | A   |   | 2/1993  | Brawn et al.      |          |
| 5,565,434 | A   |   | 10/1996 | Barfknecht et al. |          |
| 5,591,429 | A   | * | 1/1997  | Wilson et al.     | 424/93.51 |
| 5,643,883 | A   |   | 7/1997  | Marchase et al.   |          |
| 6,218,435 | B1  |   | 4/2001  | Henry et al.      |          |
| 6,410,029 | B1  | * | 6/2002  | Mukhopadhyay et al. | 424/198.1 |
| 6,489,302 | B1  |   | 12/2002 | Wiessler et al.   |          |
| 6,670,330 | B1  | * | 12/2003 | Lampidis et al.   | 514/23   |
| 2002/0035071 | A1 |   | 3/2002  | Pitha et al.      |          |
| 2002/0077300 | A1 |   | 6/2002  | Khosla et al.     |          |
| 2003/0072814 | A1 |   | 4/2003  | Maibach et al.    |          |

FOREIGN PATENT DOCUMENTS

| EP | 0565785 A1    | 10/1993 |
|----|---------------|---------|
| GR | 980100107     | 11/1999 |
| JP | 54-41384      | 4/1979  |
| WO | WO 01/82926 A1 | 11/2001 |
| WO | WO 02/058741 A2 | 8/2002 |

OTHER PUBLICATIONS

Kerr et al., abstract entitled "Normal production and increased oxidation of glucose associated with epinephrine deficiency in ketoic hypoglycemia", Pediatric Research, 8:434, 1972.*

Woodward et al., "2-desoxy-D-glucose as an inhibitor of anaerobic glycolysis in tumor tissue", Notes Biochem. Res. Found., Journal of the Franklin Institute, vol. 254, issue 3, pp. 259-60, Sep. 1952.*
Wegienka et al., abstract entitled "Use of 2-deoxy-D-glucose to stimulate function of adrenal medulla", Clinical Res., vol. XIII, No. 1, pp. 134, Jan. 1965.*
Reinhold et al., "Antitumoral action of 2-deoxy-D-glucose tetraacelate in human melanoma cells", Oncol. Rep., vol. 7, pp. 1093-97, 2000.*
Malaisse et al., "Cytotoxic action of 2-deoxy-D-glucose tetraacetate in tumoral pancreatic islet cells", Cancer Lett, 125(1-2), pp. 45-49, Mar. 1998.*
Jha et al., Reversibility of inhibition of DNA double strand break repair by 2-deoxy-D-glucose in Ehrlich ascites tumour cells, Int. J. Rad. Bio., vol. 63(4), pp. 459-487, 1993.*
Liu et al., Biochem. Pharmacol., 2002, 64:1745-51.
AFT et al., Br. J. Cancer, 2002, 87:805-12.
Chandna et al., Rad. Res., 2002, 157:516-25.
Mese et al., Anticancer Res., 2001, 21:1029-33.
Liu et al., Biochemistry, May 8, 2001, 40: 5542-7.
Yamada et al., Cancer Chemother. Pharmacol., 1999, 44: 59-64.
Dwarakanath et al., Int. J. Rad. Oncol. Biol. Phys., 1999, 43(5):1125-33.
Belfi et al., BBRC, 1999, 257:361-8.
Kalia, Indian J. Med. Res., May 1999, 109:182-7.
Haga et al., Int. J. Cancer, 1998, 76:86-90.
Chatterjee et al., Cancer Res., Nov. 15, 1997, 57:5112-16.
Kaplan et al., Cancer Res., Apr. 15, 1997, 57:1452-9.
Vivi et al., Breast Cancer Res. Treat., 1997, 43:15-25.
Tomida et al., Oncogene, 1996, 13:2699-2705.
Kraegen et al., Am. J. Physiol., 1985, 248: E353-E362.
Yun et al., Oncology Res., 1995, 7(12):583-590.
Halicka et al., Cancer Res., Jan. 15, 1995, 55:444-9.
Schaider et al., J. Cancer Res. Clin. Oncol., 1995, 121(4): 203-10.
Griffiths et al., Int. J. Biochem., 1993, 25(12):1749-55.
Kalia, Indian J. Exp. Biol., Apr. 1993, 31:312-5.
Haberkorn et al., J. Nucl. Med., Nov. 1992, 33(11):1981-7.
Cay et al., Cancer Res., Oct. 15, 1992, 52:5794-6.
Kaplan et al., Cancer Res., Mar. 15, 1991, 51:1638-44.
Kaplan et al., Cancer Res., Feb. 1, 1990, 50:544-51.
Dwarakanath et al., Indian J. Med. Res., Jun. 1990, 92:183-8.

(Continued)

Primary Examiner—James O. Wilson
Assistant Examiner—Traviss C. McIntosh, III
(74) Attorney, Agent, or Firm—Kevin R. Kaster; Photon Rao; Ted Apple

(57) ABSTRACT

The compound 2-deoxyglucose can be used to treat cancer and to improve patient outcome when administered at a therapeutically effective dose, and, optionally, co-administered with other anti-cancer drugs, or in combination with surgical resection or radiation therapy.

17 Claims, 6 Drawing Sheets

OTHER PUBLICATIONS

Ohtani et al., *Jpn. J. Exp. Med.,* Apr. 1990, 60(2):57-65.
Herr et al., *Cancer Res.,* Apr. 15, 1988, 48:2061-3.
Jain et al., *Int. J. Radiat. Oncol. Biol. Phys.,* May 1985, 11(5):943-50.
Lampidis et al., *Cancer Res.,* Feb. 1983, 43:716-20.
Steiner et al., *Cancer Lett.,* Jul. 1983, 19(3):333-42.
Sridhar et al., *Br. J. Cancer,* 1978, 37:141-4.
Myers et al., *BBRC,* 1975, 63(1):164-71.
Bessel et al., *Biochem. J.,* 1972, 128:199-204.
Bicz et al., *Arch. Immunol. Ther. Exp.,* 1967, 15(1):112-4.
AFT et al., *Proceed. AACR,* Mar. 2003, 44: Abstract No 123.
Richardson et al., *Proceed. AACR,* Mar. 2003, 44: Abstract No. 6239.
Wan et al., *FASEB J.,* Apr. 2003, 17(9):1133-4 (Web version).
Dwarakanath et al., *Indian J. Exp. Biol.,* Sep. 1999, 37(9): 865-70.
Latz et al., *Strahlenther. Onkol.,* 1993, 169(7):405-11.
Harrigan et al., *Int. J. Hyperthermia,* 1992, 8(4):475-83.
Karczmar et al., *Cancer Res.,* Jan. 1, 1992, 52:71-6.
Juling-Pohlit et al., *Strahlenther. Onkol.,* 1990,166(1):6-9.
Saydjari et al., *Invest. New Drugs,* 1989, 7:131-8.
Mack et al., *Eur J Cancer Clin. Oncol.,* Sep. 1988, 24(9): 1433-7.
Kern et al., *Surgery,* Aug. 1987, 102(2):380-5.
Gridley et al., *Int. J. Rad. Oncol. Biol. Phys.,* Mar. 1985, 11:567-74.
Dills et al., *J. Nutr.,* 1984, 114(11):2097-106.
Tannock et al., *Cancer Res.,* Mar. 1983, 43(3):980-3.
Bernal et al., *Science,* Oct. 14, 1983, 222:169-72.
Purohit, *Int. J. Rad. Oncol. Biol. Phys.,* Mar.-Apr. 1982, 8(3-4):495-9.
Laszlo et al., *JNCI,* Feb. 1960, 24 (2):267-279.
Ball et al., *Cancer Res.,* Apr. 1957, 17(3):235-9.
Sokoloff et al., *AMA Arch. Path.,* Jun. 1955, 59(6):729-32.
Abbink et al., *J. Card. Pharml.,* 2001, 37:94-100.
Adler et al., *Neuropsychopharmacology,* 2000, 22(5):545-50.
George et al., *Alcohol Clin. Exp. Res.,* May/Jun. 1994, 18(3):685-91.
Breier et al., *Arch. Gen. Psychiatry,* Jul. 1993, 50:541-50.
Breier et al., *Psychopharmacology,* 1991, 104:479-84.
Breier, *Biol. Psychiatry,* 1989, 26:438-62.
Fagius et al., *Am. J. Physiol.,* 1989, 256(6.1):E714-20.
Hansen et al., *Ped. Res.,* 1984, 18(5):490-5.
Hansen et al., *Metabolism,* Oct. 1983, 32(10):960-70.
Kerr et al., *Metabolism,* Oct., 1983, 32(10):951-9.
Thompson et al., *Metabolism,* Oct. 1981, 30(10):1015-20.
Thompson et al., *Am. J. Physiol.,* Sep. 1980, 239(3):291-295.
Thompson et al., *Science,* Dec. 9, 1977, 198:1065-8.
Woolf et al., *J. Clin. Endocr. Metab.,* 1977, 45(3):377-83.
Weber et al., *J. Surg. Res.,* 1975, 18:491-5.
Burckhardt et al., *Digestion,* 1975, 12:1-8.
Gough et al., *Gut,* 1975, 16:171-6.
Brodows et al., *J. Clin. Invest.,* Aug. 1973, 52:1841-4.
Sizonenko et al., *Ped. Res.,* 1973, 7:983-93.
Peytremann et al., *Europ. J. Clin. Invest.,* 1972, 2:432-8.
Freinkel et al., *NEJM,* Oct. 26, 1972, 287(17):841-5.
Lipman et al., *Metabolism,* 1970, 19(11):980-7.
Thomas et al., *Gut,* 1968, 9:125-8.
Grasso et al., *J. Clin. Endocr.,* 1968, 28:535-42.
Wegienka et al., *Metabolism,* Mar. 1967, 16(3):245-56.
Wegienka et al., *J. Clin. Endocr.,* Jan. 1966, 26:37-45.
Duke et al., *Lancet,* Oct. 30, 1965, 871-6
Harlan et al., *J. Clin. Endrocrinol. Metab.,* Jan. 1963, 23:41-9.
Laszlo et al., *J. Clin. Invest.,* Jan. 1961, 40:171-6.
Landau et al., *JNCI,* Sep. 1958, 21(3):485-494.
Mohanti et al., *Int. J. Rad. Oncol. Biol. Phys.,* 1996, 35(1): 103-11.
Blough et al., JAMA, Jun. 29, 1979, 241(26): 2798-2801.
Song et al., *Cancer Res.,* Dec. 1978, 38: 4499-4503.
Song et al., *Br. J. Cancer,* 1978, Suppl. III:136-140.
Song et al., *JNCI,* Sep. 1976, 57(3): 603-605.
Clavo et al., *J. Nuc. Med.,* Sep. 1995, 36(9):1625-1632.
Mesmer et al., *Biochem. Mol. Biol. Int.,* Oct. 1996, 40(2): 217-33.
Shen et al., May 1987, *Proc. Natl. Acad. Sci. USA 84:* 3278-3282.
Colofiore et al., Oct. 1982, *Cancer Res. 42:* 3934-3940.
Hughes et al., 1989, *Cancer Res. 49:* 4452-4454.
Mese et al., 2001, *Anticancer Res. 21*(2A): 1029-33.
Teicher et al., Jan. 1981, *Cancer Res. 41:*73-81.
Mazurek et al., 1997, *J. Bioener. Biomem.* 29(4): 315-330.
Jensen et al., 1992, *Cancer Chemother. Pharmacol. 31:*46-52.
Kim et al., Apr. 14, 1978, *Science 200:*206-207.
Lam et al., 1999, *Anti-cancer Drugs 10:*171-178.
Bessell et al., 1972, *Biochem J. 128:*199-204.
Bessell et al., 1973, *Eur. J. Cancer 9:*463-470.

\* cited by examiner

A.

B. FIGURE 1. Continued
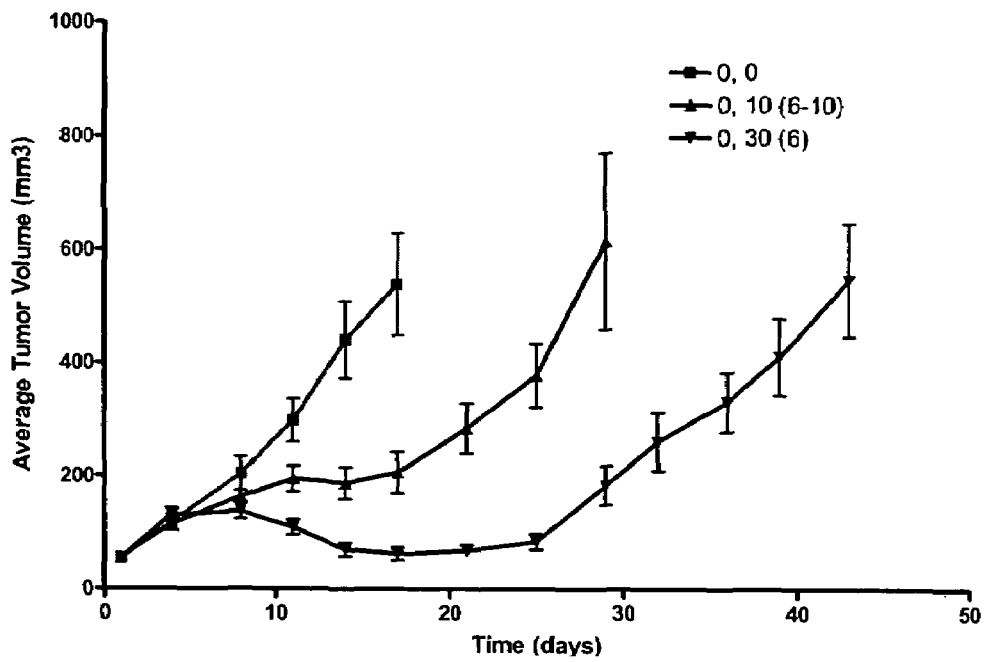
C.
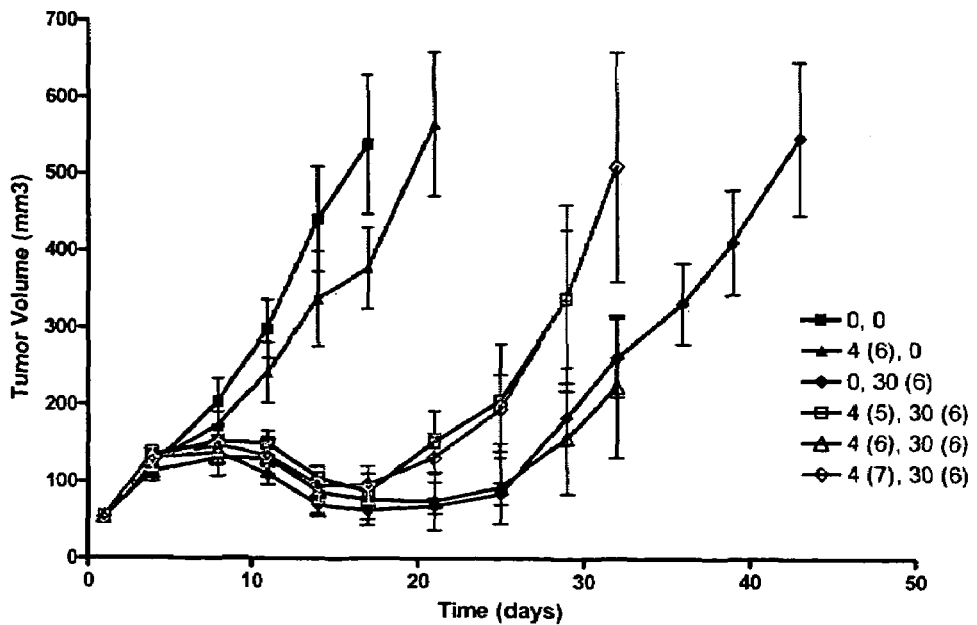

FIGURE 1, Continued
D.
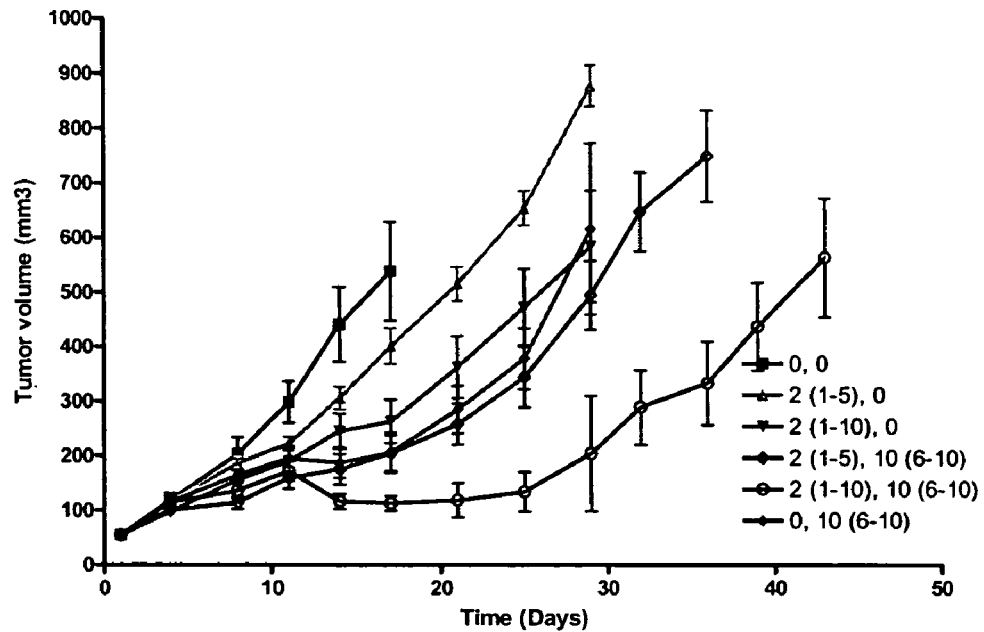
E.
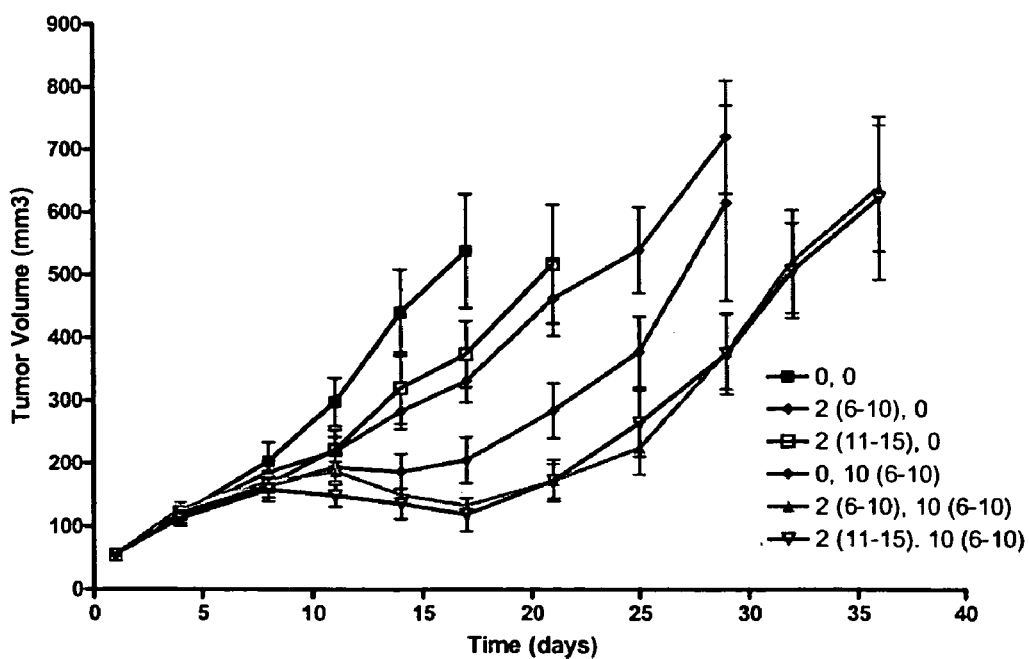

FIGURE 1, Continued
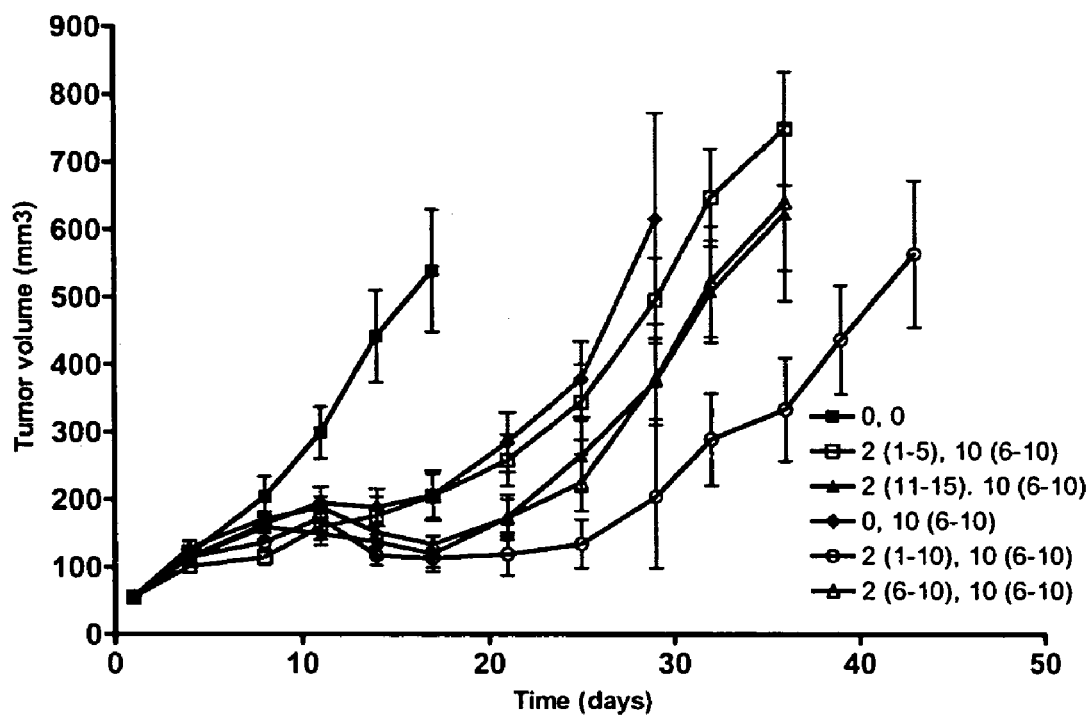

R= CH₃, CH₂F, CHF₂, CF₃

R= CH₃, CH₂F, CHF₂, CF₃

R= CH₃, CH₂F, CHF₂, CF₃

R= CH₃, CH₂F, CHF₂, CF₃

FIGURE 2, Continued
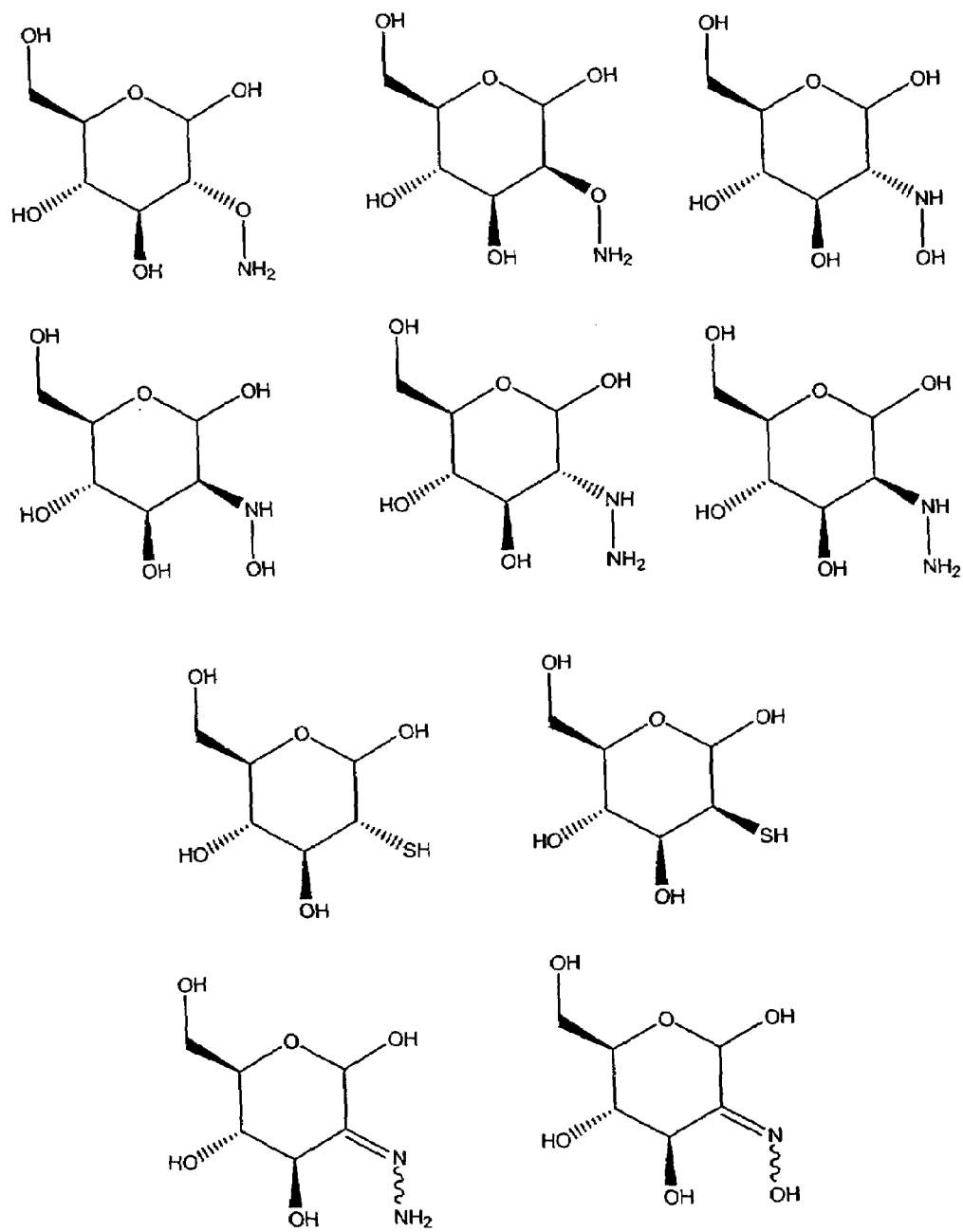
wavy bond denotes E or Z isomer of double bond

TREATMENT OF CANCER WITH 2-DEOXYGLUCOSE

CROSS-REFERENCE TO RELATED APPLICATION

This application claims benefit of U.S. provisional patent application Ser. Nos. 60/439,266, filed 10 Jan. 2003; 60/458,665 and 60/458,846, both filed 28 Mar. 2003, 60/460,012, filed 2 Apr. 2003; and 60/496,163, filed 18 Aug. 2003, each of which is incorporated herein by reference.

BACKGROUND OF THE INVENTION

"Cancer" generally refers to one of a group of more than 100 diseases caused by the uncontrolled, abnormal growth of cells that can spread to adjoining tissues or other parts of the body. Cancer cells can form a solid tumor, in which the cancer cells are massed together, or exist as dispersed cells, as in leukemia. Normal cells divide (reproduce) until maturation is attained and then only as necessary for replacement of damaged or dead cells. Cancer cells are often referred to as "malignant", because they divide endlessly, eventually crowding out nearby cells and spreading to other parts of the body. The tendency of cancer cells to spread from one organ to another or from one part of the body to another distinguishes them from benign tumor cells, which overgrow but do not spread to other organs or parts of the body. Malignant cancer cells eventually metastasize and spread to other parts of the body via the bloodstream or lymphatic system, where they can multiply and form new tumors. This sort of tumor progression makes cancer a deadly disease. Although there have been great improvements in the diagnosis and treatment of cancer, many people die from cancer each year, and their deaths are typically due to metastases and cancers that are resistant to conventional therapies.

Most drug-mediated cancer therapies rely on poisons, called cytotoxic agents, selective for dividing cells. These drugs are effective, because cancer cells generally divide more frequently than normal cells. However, such drugs almost inevitably do not kill all of the cancer cells in the patient. One reason is that cancer cells can acquire mutations that confer drug resistance. Another is that not all cancer cells divide more frequently than normal cells, and slowly-dividing cancer cells can be as, or even more, insensitive to such poisons as normal cells. Some cancer cells divide slowly, because they reside in a poorly vascularized, solid tumor and are unable to generate the energy required for cell division. As a tumor grows, it requires a blood supply and, consequently, growth of new vasculature. The new vasculature that supports tumor growth is often disordered, leaving significant regions of the tumor under-vascularized and even the vascularized regions subject to intermittent blockage. These under-vascularized and blocked regions of the tumor become hypoxic—they have a lower oxygen concentration than the corresponding normal tissue, and the cells in them exhibit slower rates of division. Thus, the median oxygen concentration of only ten percent of solid tumors falls in the normal range of 40–60 mm Hg, and fifty percent of solid tumors exhibit median oxygen concentrations of less than 10 mm Hg.

In addition to rendering cytotoxic agents that target rapidly dividing cells less effective, the hypoxic environment of the tumor can lead to failures in therapy in other ways. First, oxygen is required for the therapeutic action of some cancer drug and radiation therapies. Second, cancer drugs typically reach a tumor via the bloodstream, and poor vascularization leads to poor distribution of cancer drugs to the hypoxic regions of a tumor. For all of these reasons, the hypoxic areas of the tumor represent a significant source of cancer cells resistant to therapy. Not surprisingly, then, low tumor oxygen levels are associated with a poor response to therapy, increased metastases, and poor survival.

Cancer cells require energy to support their rapid rates of cell division, and even the more slowly dividing cancer cells in the hypoxic regions of tumors require energy to survive (and the lack of oxygen deprives them of energy generation via the Krebs cycle, which requires oxygen). Not surprisingly, then, many cancer cells exhibit, relative to normal cells, increased glucose transport and glycolysis, because energy can be generated by glycolysis in the absence of oxygen. Moreover, increased uptake of glucose is one of the most common signs of a highly malignant tumor. Thus, the reference Dickens, 1943, *Cancer Research* 3:73, reported that "the typical intact cancer cell exhibits an unusual ability to utilize glucose by the process of anaerobic glycolysis through lactate". Given the increased glycolysis in cancer cells, inhibition of anaerobic glycolysis by metabolic poisons such as 2-deoxy-D-glucose (also known as 2-desoxy-D-glucose and 2-DG; for synthetic methods, see Bergmann, 1922, *Deutsch. Chem. Ges.* 56:158–60; Cramer, 1952, *Franklin Inst.* 253:277–80; and Japan patent publication No. 54-041384) has been studied as a means to kill cancer cells preferentially (see McDonald, 1952, *Cancer Research* 351–353).

2-DG has been reported to inhibit glycolysis in and growth of cancer cells (see Woodward, 1954, *Cancer Res.* 14:599–605; Barban, 1961, *J. Biol. Chem.*, 236(7):1887–90; Myers, March 1975, *Biochem Biophys Res Commun.* 63(1): 164–71; Steiner, July 1983, *Cancer Lett.* 19(3):333–42; Karczmar, January 1992, *Cancer Res.* 52(1):71–76; Kern, August 1987, *surgery* 102(2):380–85; Kaplan, February 1990, *Cancer Res.* 50(3):544–51; Kaplan, March 1991, *Cancer Res.* 51:1638–44; Haberkorn, November 1992, *J. Nucl. Med.* 33(11):1981–87; Jha, April 1993, *Int. J. Radiat. Biol.* 63(4):459–67; Malaisse, March 1998, *Cancer Lett.* 125:4549; and Aft et al., 2002, *Br. J. Cancer* 87: 805–812). 2-DG has also been reported to retard tumor growth in some animal models (Sokoloff, 1955, *A.M.A. Arch. Path.* 729–732; Ball, 1957, *Cancer Res.* 17:235–39; Laszlo, February 1960, *J. Natl. Canc. Inst.* 24(2):267–281; Dills, November 1984, *J. Nutr.* 114(11):2097–106; Kern, 1987, *Surgery* 102(2): 380–385; and Cay et al., 1992, *Cancer Res.* 52(20): 5794–5796). 2-DG was first administered to human cancer patients in the 1950s (see Landau, 1958, *J. Natl. Canc. Inst.* 21:485–494) by single i.v. infusion without any apparent therapeutic effect.

2-DG has been studied in combination with radiation (see Purohit, March 1982, *Int. J. Radiat. Oncol. Biol. Phys.* 8:495–99; Tannock, March 1983, *Cancer Res.*, 43(3):980–83; Jain, May 1985, *Int. J. Radiat. Oncol. Biol. Phys.* 11(5):943–50; Gridley, 1985, *Oncology* 42(6):391–98; Dwarakanath, May 1987, *Int. J. Radiat. Oncol. Biol. Phys.* 13(5):741–46; Dwarakanath, March 1999, *Int. J. Radiat. Oncol. Biol. Phys.* 43(5):1125–33; Dwarkanath, July 2001, *Int. J. Radiat. Oncol. Biol. Phys.* 50(4):1051–61; Kalia, April 1993, *Indian J. Exp. Biol.* 31(4):312–15; Latz, July 1993, *Strahlenther Onkol* 169(7): 405–11; Mohanti, April 1996, *Int. J Radiat. Oncol. Biol. Phys.* 35(1):103–11; Kalia, May 1999, *Indian J. Med. Res.* 109:182–87; and Yeung, 11 Dec. 2001, PCT WO 02/58741).

2-DG has been studied in combination with other cytotoxins and anti-cancer drugs (see Lampidis, February 1983, *Cancer Res.* 43:716–20; Bernal, October 1983, *Science*

222:169–72; Herr, April 1988, *Cancer Res.* 48:2061–63; Liu, May 2001, *Biochemistry*, 840(18):5542–47; Saydjari, July 1989, *Invest. New Drugs* 7:131–38; Saydjari, 1989, *Pancreas*, 4:38–43; Haga, March 1998, *Int. J. Cancer* 76(1):86–90; Belfi, April 1999, *Biochem. Biophys. Res. Commun.* 257(2):361–68; Yamada, 1999, *Cancer Chemother. Pharmacol.* 44(1):59–64; Halicka, January 1995, *Cancer Res.* 55(2):444–49; Yun, 1995, *Oncol. Res.* 7(12):583–90; Schaider, 1995, *J. Cancer Res. Clin. Oncol.* 121(4):203–10; Ben-Horin, July 1995, *Cancer Res.* 55(13): 2814–21; Tomida, November 1996, *Inter J. Cancer Res* 68(3):391–96; Reinhold, September 2000, *Oncol. Rep.*, 7(5):1093–97; Mese, March 2001, *Anticancer Res.* 21:1029–33; Lampidis, 2 Mar. 2001, PCT WO 01/82926 and U.S. Pat. No. 6,670,330).

However, after more than five decades of study, 2-DG has not been approved for the treatment of cancer in the United States or Europe. There remains a need for methods of treating cancer with 2-DG. The present invention meets that and other needs.

SUMMARY OF THE INVENTION

In a first aspect, the present invention provides a method of treating cancer, which method comprises administering to a mammal a therapeutically effective dose of 2-deoxy-D-glucose (2-DG). In particular, the invention provides a method of treating cancer by administering to a mammal in need of treatment for a cancer a therapeutically effective dose of 2-DG, where the therapeutically effective dose is obtained by administering 2-DG at a frequency greater than one day per week. According to the invention, 2-DG is administered in a daily dose in the range of about 1 mg of 2-DG per kg of patient weight (1 mg/kg)) to about 1 g/kg for multiple days. In one embodiment, the daily dose is a dose in the range of about 5 mg/kg to about 500 mg/kg. In another embodiment, the daily dose is about 10 mg/kg to about 250 mg/kg. In another embodiment, the daily dose is about 25 mg/kg to about 150 mg/kg. The daily dose of 2-DG can be administered once per day (qday) or divided into subdoses and administered in multiple doses, e.g., twice (bid), three times (tid), or four times (qid) per day.

To achieve the desired therapeutic effect, 2-DG must be administered for multiple days at the therapeutically effective daily dose. Thus, therapeutically effective administration of 2-DG to treat cancer requires periodic (e.g., daily) administration that continues for a period ranging from three days to two weeks or longer. In one embodiment, the treatment is continued for one to three months. Typically, 2-DG will be administered for at least three consecutive days, often for at least five consecutive days, more often for at least ten, and sometimes for twenty, thirty, forty or more consecutive days. While consecutive daily doses are a preferred route to achieve a therapeutically effective dose, a therapeutically beneficial effect can be achieved even if the drug is not administered daily, so long as the administration is repeated frequently enough to maintain a therapeutically effective concentration of the drug in the patient. For example, one can dose every other day (qod), every third day, or, if higher dose ranges (250 mg 2-DG/kg of patient weight and higher) are employed, once a week (qweek), provided, however, that in all instances the drug is administered multiple times. In a second aspect, the present invention provides a pharmaceutically acceptable formulation of 2-DG useful in the methods of the present invention.

The 2-DG formulations of the invention include, but are not limited to, those suitable for oral administration and for parenteral injection.

In a related aspect, the invention provides the use of 2-DG for treatment of cancer in a mammal. In another related aspect, the invention provides the use of 2-DG in the manufacture of a medicament for the treatment of cancer. In another related aspect, the invention provides the use of 2-DG in the manufacture of a medicament for use in combination with other anticancer agents for the treatment of cancer. In another related aspect, the invention provides the use of 2-DG in the manufacture of a medicament for use in combination with a metabolic inhibitor for the treatment of cancer. In one embodiment, the medicament is administered daily for at least three days in a one week period. In one embodiment, the medicament is administered orally. In one embodiment, the medicament is a tablet or capsule. In another embodiment, the medicament is a liquid. In one embodiment, the medicament is a liquid that contains 2-DG at a concentration in the range of 1 to 450 mg/mL, more preferably in the range of 50 to 250 mg/mL and optionally contains a preservative. In one embodiment, the medicament is a tablet, pill, capsule, or sachet containing from about 50 mg to about 5 g of 2-DG.

In a third aspect, the present invention provides a method of treating or preventing cancer, which method comprises administering to a mammal a therapeutically effective dose of 2-DG. In one embodiment, the method comprises administering to a mammal a therapeutically effective dose of 2-DG in combination with another anti-cancer agent. In one embodiment, the method comprises administering to a mammal a therapeutically effective dose of 2-DG in combination with surgery and, optionally, administration of another anti-cancer agent. In one embodiment, the method comprises administering to a mammal a therapeutically effective dose of 2-DG in combination with radiation therapy and, optionally, administration of another anti-cancer agent. In one embodiment, the cancer is breast cancer, colon cancer, non-small cell lung cancer, or prostate cancer. In one embodiment, the cancer is a multi-drug resistant cancer or a cancer that is otherwise refractory to treatment. In one embodiment, the cancer is a taxane-resistant cancer, and the method comprises administration of a taxane and 2-DG at a therapeutically effective dose.

In a related aspect, the present invention provides methods for treating cancer that involve a preliminary assessment of the cancer patient to determine the degree of susceptibility of the patient's cancer to 2-DG mediated drug therapy. These and other aspects and embodiments of the invention are described in more detail below.

DETAILED DESCRIPTION OF THE INVENTION

Figure 1:
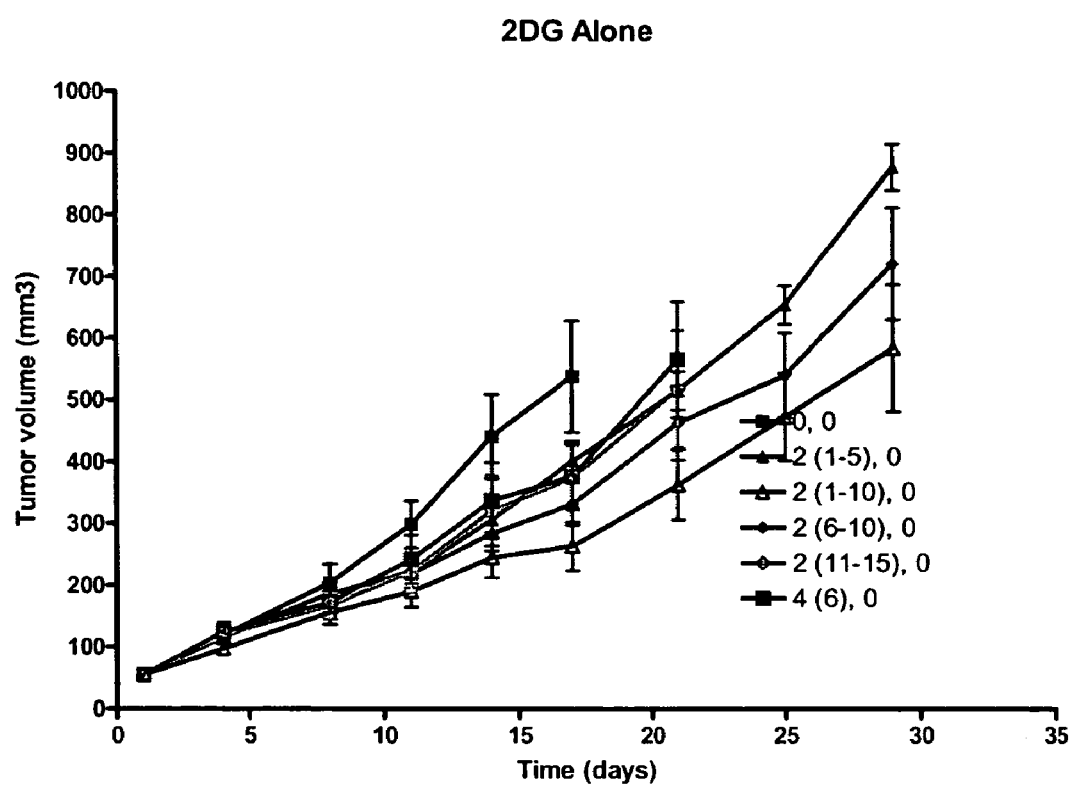
FIG. 1, panels A–F, shows results of a 2-DG/paclitaxel dosing study in a mouse MV522 xenograft model.

The present invention provides methods of treating cancer by administering a therapeutically effective dose of 2-DG, alone or in combination with other anti-cancer therapies, including surgical resection, radiation therapy, and drug therapy. To aid in the appreciation of the invention, this description is divided into the following topics: (i) therapeutically effective administration of 2-DG; (ii) co-administration with other anti-cancer agents; (iii) co-administration with metabolic inhibitors and other agents; (iv) patient assessment for 2-DG treatment (v) treatment of particular cancers; and (vii) formulation and packaging of 2-DG.

Therapeutically Effective Administration of 2-DG

While the effect of the administration of 2-DG on cancer cells and cancer patients has been studied for many years, 2-DG has never been approved for the treatment of cancer, because no one has discovered a therapeutically effective dose or administration regimen for the compound. The present invention arose in part from the discoveries that the desired therapeutic effect can be achieved only by repeated administration of the compound in an effective dose range. In one aspect, the invention provides a method of treating cancer in a patient by administering a therapeutically effective dose of 2-DG to the mammal, where the therapeutically effective dose obtained by administering 2-DG at a frequency greater than one day per week. While "patient" typically refers to a human, those of skill in the art will appreciate that the methods and compositions of the invention can be used to treat cancer in any mammal, including non-human primates and experimental models of human cancers. In one embodiment of the invention the patient is a human patient. As used herein, "treating" cancer (or treating a patient with cancer) refers to taking steps to obtain beneficial or desired results, including but not limited to, alleviation or amelioration of one or more symptoms of the cancer, diminishment of extent of disease, delay or slowing of disease progression, amelioration, palliation or stabilization of the disease state, partial or complete remission, prolonged survival and other beneficial results known in the art.

In accordance with the methods of the present invention, 2-DG is administered in a daily dose in the range of about 1 mg of 2-DG/kg of patient weight to about 1 g/kg of 2-DG per patient weight. For treatment of human patients, the maximum daily dose is preferably not greater than 500 mg/kg patient weight and, accordingly, 2-DG is administered in a daily dose in the range of about 1 mg of 2-DG/kg of patient weight to about 500 mg/kg of 2-DG per patient weight. In one embodiment, 2-DG is administered in a daily dose in the range of about 5 mg/kg to about 500 mg/kg of 2-DG per body weight of the patient to be treated. In another embodiment, the therapeutically effective dose is a daily dose of about 10 mg/kg to about 250 mg/kg of 2-DG per body weight of the patient to be treated. In another embodiment, the therapeutically effective dose is about 25 mg/kg to about 150 mg/kg of 2-DG per body weight of the patient to be treated. In another embodiment, the therapeutically effective dose is about 25 mg/kg to about 150 mg/kg of 2-DG per body weight of the patient to be treated.

To achieve therapeutic effectiveness, the therapeutically effective daily dose of 2-DG is usually administered multiple times to the patient. In one embodiment, 2-DG is administered daily for a period of time. Typically, daily administration for at least 3 consecutive days will be employed. In related embodiments, administration is for at least 5 consecutive days, at least 7 consecutive days, or at least 10 consecutive days. Depending on the dose, formulation, and route of administration selected by the practitioner and the convenience of the patient, the entire daily dose may be administered once daily, or the daily dose may be administered in multiple smaller doses through the course of a day (including by infusion with a pump or intravenous administration). For example, the dose may be divided into two smaller doses and administered twice daily, or divided into three smaller doses and administered thrice daily. It will be apparent to the reader that, as used herein, "daily" administration is not limited to one administration per day but can include multiple administrations.

Administration schedules other than consecutive daily administration can also be used. Administration once every other day (qod) is particularly convenient, and administration once every third day, or once a week may be appropiate in some instances, but in any event, 2-DG is repeatedly administered over a period of time. For example, whether administration is daily (including, as noted, a divided daily dose), every other day, or less frequently, in one embodiment 2-DG is administered at least 2 days per week for at least two, three, four, five or at least six consecutive weeks, or, alternatively, for at least two, three, four, five or at least six weeks within a six-month period, or, alternatively, for at least two, three, four, five or at least six weeks within a twelve-month period. In one embodiment, 2-DG is administered at least 3 days per week for at least two, three, four, five or at least six consecutive weeks, or, alternatively, for at least two, three, four, five or at least six weeks within a six-month period, or, alternatively, for at least two, three, four, five or at least six weeks within a twelve-month period. In one embodiment 2-DG is administered at least 10 days per month, optionally at least 20 days per month, for at least one month or at least two, three, four, five or at least six consecutive months, or, alternatively, at least one, two, three, four, five or at least six months in a 6-month period.

For optimum treatment benefit, the administration of the therapeutically effective dose is continued for multiple days, typically for at least three consecutive days, and often for at least five to ten consecutive days, or for a week, or for several weeks or more. Thus, a patient may be administered 2-DG in accordance with the present methods for several days, a week, a month, two months, three months, six months, or a year or longer.

Consistent with administration regimens of other anticancer agents, 2-DG may be administered in multiple "rounds" of administration. For example, in some embodiments, 2-DG may be administered once daily for at least three to ten, or at least five to ten consecutive days, and such three to ten- or five to ten-day treatments may be repeated once, twice, or three or more times, sometimes with a no-treatment (with 2-DG) period ranging from one to several weeks between each multiple-day treatment. Similarly, in some embodiments, 2-DG is administered every other day for two to ten administrations, more often three to ten administrations, or five to ten administrations, and such two, three or five to ten administrations qod may be repeated once, twice, or three or more times with a no-treatment (with 2-DG) period ranging from one to several weeks between each multiple-day treatment. Other multiple-round schedules for administration will be apparent to the skilled practicioner quided by this disclosure.

In one aspect, "administering a therapeutically effective dose or regimen of 2-DG" refers to (i) administering 2-DG in the ranges stated (e.g., 1 mg to 1 g of 2-DG per kg of patient weight, typically 25 to 150 mg of 2-DG per kg of patient weight) for a specified minimum number of days within a specified time period, wherein the administration of 2-DG has a therapeutic effect on the cancer in the patient. Illustrative therapeutically effective dose regimens for 2-DG include those described herein, such as administration of 2-DG for 3 consecutive days, 5 consecutive days, 7 consecutive days, 10 consecutive days, at least 3 days per week, at least 3 days per week for one month, at least 10 days per month, and at least 20 days per month.

In optimizing a 2-DG treatment regimen according to the present invention, the dose and frequency of 2-DG administration can be selected to achieve a maximal sustained area under the plasma concentration curve (AUC) over the course of treatment. The theoretically optimal dosing regimen will result in a maximal exposure of the tumor cells to 2-DG, as measured by AUC, while minimizing the maximal plasma concentration ($C_{max}$) for any single administration. A higher $C_{max}$ will contribute to toxicity while the AUC will determine efficacy. As is understood in the art for other cancer therapeutic drugs, treatment with 2-DG may be suspended temporarily if toxicity is observed, or for the convenience of the patient, without departing from the scope of the invention, and then resumed. 2-DG toxicity may result in symptoms consistent with hypoglycemia (including sweating, irritability or nausea). In re-treatment regimens, the dose can be adjusted to reflect patient tolerance of the prior treatment. In any event, as toxicity is observed during repeat administration, dosing can be temporarily stopped as severe symptoms are observed. The period of temporary halting of administration (drug holiday) can be ended at the time when the first organ of toxicity (brain) no longer contains significant concentrations of 2-DG (which can be measured or determined indirectly by cessation of symptoms). Therefore, an intermittent dosing period can be defined not only by specific days but individualized by drug holidays that are based on symptoms and normal organ clearance of 2-DG.

In one embodiment, the 2-DG is administered in a formulation that doesn't contain glucose. In one embodiment, the patient fasts from 8 to 16 hours prior to the administration of the 2-DG. In one embodiment, the patient is maintained on a low glucose diet during the time period when 2-DG is administered. In one embodiment, of the invention, 2-DG is administered to a patient on a low carbohydrate diet, such as the Atkins diet. Without intending to be bound by a particular mechanism, consumption of a low carbohydrate diet results in decreased glucose available to the body, making the cells in hypoxic regions of tumors in that body even more "starved" for glucose and thereby rendering those cells even more susceptible to 2-DG (i.e., because the hypoxic cells are highly dependent on glucose for energy; the less glucose there is, the less energy there is, and the lower energy levels make the cell even more susceptible to 2-DG, which blocks energy production from glycolysis). Moreover, a low carbohydrate (and optionally high fat and/or high protein) diet will force the body to utilize fat for the generation of energy, resulting in the generation of ketone bodies. Ketone bodies are preferred by the brain for energy production over glucose, so an increase in ketone bodies decreases the brain's dependence on glucose and therefore decreases its sensitivity to 2-DG (i.e., if the brain can generate sufficient energy from ketone bodies, then the brain is not distressed by the 2-DG-mediated block on the glycolytic pathway). Because 2-DG build-up in the brain can lead to toxicity (typically manifested by symptoms associated with hypoglycemia), the production of ketone bodies in effect serves to protect the brain from 2-DG, allowing one to give higher doses of 2-DG or administer 2-DG continuously for longer periods of time. Finally, ketone bodies may have anti-cancer effects in and of themselves, so the production of ketone bodies can increase the therapeutic efficacy of an anti-cancer regimen with 2-DG.

2-DG can be administered in any number of ways known to those of skill in the art (e.g., including oral, parenteral, intramuscular, topical, or subcutaneous routes), but is generally administered orally or by parenteral injection (e.g., intravenous administration). Although intravenous administration is generally preferred for anticancer agents, surprisingly, oral administration of 2-DG can be equally efficacious and is better tolerated (less toxic) than i.v. administration. This discovery enables design of treatment regimens in which 2-DG is administered more frequently and/or at higher doses than otherwise possible. Thus, in one preferred embodiment of the invention, the 2-DG is administered orally, and multiple doses are administered over a period of time as described above.

Using this therapeutically effective dosing and administration regimen, practitioners of skill in the art can significantly improve treatment outcomes achieved with currently used cancer therapies (including surgical resection, radiation therapy, and drug therapies), as well as with new drug therapies in development. In one important aspect, the present invention provides new methods for treating cancer by using other anti-cancer drugs in combination with 2-DG, as discussed in the following section.

Co-administration with Other Anti-cancer Agents

In accordance with the methods of the invention, 2-DG can be co-administered in combination with other anticancer agents ("anticancer agent"). Without intending to be bound by any particular mechanism or effect, such co-administration can in some cases provide one or more of several unexpected benefits including:

(i) co-administration of 2-DG and the anticancer agent has a synergistic effect on induction of cancer cell death;

(ii) co-administration provides a better therapeutic result than administration of the anticancer agent alone, e.g., greater alleviation or amelioration of one or more symptoms of the cancer, diminishment of extent of disease, delay or slowing of disease progression, amelioration, palliation or stabilization of the disease state, partial or complete remission, prolonged survival or other beneficial therapeutic results;

(iii) co-administration of 2-DG increases the sensitivity of cancer cells to the anticancer agent, allowing lower doses of the agent to be adminstered to the patient or allowing an agent to be used for treatment of cells otherwise resistant to the agent or otherwise refractory to treatment;

(iv) co-administration of 2-DG and the anticancer agent increases killing of cells in hypoxic regions of tumors that are not efficiently killed by the agent alone.

As used herein, 2-DG is "co-administered" with another anticancer agent (also referred to herein as, "Agent") when the 2-DG and Agent are administered as part of the same course of therapy. In one embodiment, 2-DG is first administered prior to administration of the Agent, (i.e., the initiation of the other cancer therapy), and treatment with 2-DG is continued throughout the course of administration of the Agent (i.e., the course of the other therapy). In another embodiment, 2-DG is administered after the initiation or completion of the other cancer therapy. In other embodiments, 2-DG is first administered contemporaneously with the initiation of the other cancer therapy. In one embodiment, 2-DG is first administered prior to administration of the Agent, and treatment with 2-DG is continued after the cessation of administration of the Agent. In one embodiment, 2-DG is first administered prior to administration of the Agent, and treatment with 2-DG is continued during part of the period of administration of the Agent. For certain drugs, such as certain topoisomerase inhibitors, the 2-DG administration may be initiated and completed prior to the administration of the second drug.

Anticancer drug therapy today typically involves multiple rounds, or "cycles," of administration of the anti-cancer agent(s). In the context of administering 2-DG, each cycle of administration (as well as a complete set of cycles) can be viewed as administration of a second drug. Thus, 2-DG can be administered in any or all of the multiple cycles of treatment with the other Agent; in general, 2-DG will be given on a daily basis for at least two or more days during each cycle. In one aspect of the invention, 2-DG is co-administered with the Agent according to a schedule repeated at each round. For example, in one conventional therapy, paclitaxel is administered at 135 mg/m$^2$ by IV as a 24-hour infusion once every 21 days, e.g., Days 21, 42, 63, and 84 of a course of treatment. In this example, each round of paclitaxel administration can be accompanied by 2-DG co-administration which is concurrent with the paclitaxel administration (e.g., 2-DG is administered on Days 21, 42, 63, and 84), precedes the paclitaxel administration (e.g., 2-DG is administered on Days 20, 41, 62, and 83), and immediately after the paclitaxel administration (e.g., 2-DG is administered on Days 22, 43, 64, and 85; or if administered qod during roughly the same periods, Days 21 and 23; 42 and 44, 63 and 65; and 84 and 86). For convenience, however, and particularly if the Agent is administered by IV infusion, the physician may omit the preceding day dose of 2-DG for the first cycle. Alternatively, 2-DG may be administered continuously throughout multiple cycles of administration of the anticancer Agent (e.g., in the paclitaxal example, daily beginning on or before day 21 and extending until the end of therapy; every other day beginning on or before day 21 and extending until the end of therapy, etc.). It will be understood that the aforelisted examples are for illustration only, and not intended to limit the invention in any fashion. Those of skill in the art will also appreciate that in many cases the schedule of co-admistration may differ in the first therapeutic cycle for the convenience of the patient (e.g., no 2-DG administration prior to the first administration of paclitaxel).

In one embodiment, 2-DG is administered with an anti-cancer agent that is more effective when ATP levels in the cancer cell are low. In this embodiment, the therapy of the invention optionally includes an assay or test to measure ATP levels (or a surrogate marker) in the tumor to be treated. 2-DG acts in part by reducing the ATP available to the cancer cell. Thus, in one aspect of the invention, 2-DG is administered once in an amount effective for reducing ATP levels in the tumor and administered again only after ATP levels begin to rise again; thereafter, 2-DG is administered to maintain ATP at a low level in the tumor. Thus, a single dose of 2-DG that reduces ATP in a cancer cell can have a therapeutic effect. As but one example, the DNA damage induced by radiation therapy and by certain drug therapies, such as treatment with an alkylator or other DNA modifier, requires ATP for repair. Consequently, administration of 2-DG in accordance with the methods of the present invention can improve patient outcomes when conducted concurrently with such therapies. In one embodiment of this method, the 2-DG is administered contemporaneously with the administration of the DNA damaging agent, and administration of 2-DG is stopped when the other treatment is stopped or within a few days thereafter.

In a related embodiment, 2-DG is administered in combination with another anti-cancer agent in accordance with the methods of the invention to treat a multiple drug resistant tumor, and this treatment method can optionally include a step to diagnose whether a tumor is multiply drug resistance. This step can simply be the administration of a drug and the observation that the cancer appears to be resistant to the drug or a diagnostic test for the presence of an RNA, a protein, or an activity associated with multiple drug resistance. Multiple drug resistance can arise from the expression of certain proteins, including P-glycoprotein (PGP), multidrug-resistance protein (MRP), and lung-resistance protein (LRP). PGP causes resistance to anthracyclines (such as doxorubicin, daunorubicin, and epirubicin), mitxantrone, vinca alkaloids (vinblastine, vincristine), etoposide, the taxanes (paclitaxel, docetaxel), and actinomycin D; MRP causes resistance to anthracyclines, vinca alkaloids, and etoposide; and LRP causes resistance to anthracyclines, mitoxantrone, cisplatin (CDDP), and certain alkylating agents. In one embodiment, the therapeutic method of the invention comprises administering to a patient having a multiple-drug-resistant cancer a therapeutically effective regiment of 2-DG together with another anti-cancer agent selected from those agents to which the multiple-drug resistant tumor is otherwise resistant.

In another embodiment, 2-DG is administered with an anti-cancer agent that acts, either directly or indirectly, to inhibit hypoxia-inducible factor 1 alpha (HIF1a) or to inhibit a protein or enzyme, such as a glucose transporter or VEGF, whose expression or activity is increased upon increased HIF1 levels. HIF1 inhibitors suitable for use in this embodiment of the invention include P13 kinase inhibitors; LY294002; rapamycin; histone deacetylase inhibitors such as [(E)-(1S,4S,10S,21 R)-7-[(Z)-ethylidene]-4,21-diisopropyl-2-oxa-12,13-dithia-5,8,20,23-tetraazabicyclo-[8,7,6]-tricos-16-ene-3,6,9,19,22-pentanone (FR901228, depsipeptide); heat shock protein 90 (Hsp90) inhibitors such as geldanamycin, 17-allylamino-geldanamycin (17-AAG), and other geldanamycin analogs, and radicicol and radicicol derivatives such as KF58333; genistein; indanone; staurosporin; protein kinase-1 (MEK-1) inhibitors such as PD98059 (2'-amino-3'-methoxyflavone); PX-12 (1-methylpropyl 2-imidazolyl disulfide); pleurotin PX478; quinoxaline 1,4-dioxides; sodium butyrate (NaB); sodium nitropurruside (SNP) and other NO donors; microtubule inhibitors such as novobiocin, panzem (2-methoxyestradiol or 2-ME2), vincristines, taxanes, epothilones, discodermolide, and derivatives of any of the foregoing; coumarins; barbituric and thiobarbituric acid analogs; camptothecins; and YC-1, a compound described in Biochem. Pharmacol., 15 Apr. 2001, 61(8):947–954, incorporated herein by reference, and its derivatives.

In another embodiment, 2-DG is administered with an anti-angiogenic agent, including but not limited to anti-angiogenic agents selected from the group consisting of angiostatin, an agent that inhibits or otherwise antagonizes the action of VEGF, batimastat, captopril, cartilage derived inhibitor, genistein, endostatin, interleukin, lavendustin A, medroxypregesterone acetate, recombinant human platelet factor 4, Taxol, tecogalan, thalidomide, thrombospondin, TNP-470, and Avastin. Other useful angiogenesis inhibitors for purposes of the combination therapies provided by the present invention include Cox-2 inhibitors like celecoxib (Celebrex), diclofenac (Voltaren), etodolac (Lodine), fenoprofen (Nalfon), indomethacin (Indocin), ketoprofen (Orudis, Oruvail), ketoralac (Toradol), oxaprozin (Daypro), nabumetone (Relafen), sulindac (Clinoril), tolmetin (Tolectin), rofecoxib (Vioxx), ibuprofen (Advil), naproxen (Aleve, Naprosyn), aspirin, and acetaminophen (Tylenol). In addition, because pyruvic acid plays an important role in angiogenesis, pyruvate mimics and glycolytic inhibitors like halopyruvates, including bromopyruvate, can be used in combination with an anti-angiogenic compound and 2-DG to treat cancer. In another embodiment, 2-DG is administered with an anti-angiogenic agent and another anti-cancer agent, including but not limited to a cytotoxic agent selected from the group consisting of alkylators, Cisplatin, Carboplatin, and inhibitors of microtubule assembly, to treat cancer.

In addition to the combination of 2-DG with the agents described above, the present invention provides a variety of synergistic combinations of 2-DG and other anti-cancer drugs. Those of skill in the art can readily determine the anti-cancer drugs that act "synergistically" with 2-DG as described herein. For example, the reference Vendetti, "Relevance of Transplantable Animal-Tumor Systems to the Selection of New Agents for Clinical Trial," Pharmacological Basis of Cancer Chemotherapy, Williams and Wilkins, Baltimore, 1975, and Simpson Herren et al., 1985, "Evaluation of In Vivo Tumor Models for Predicting Clinical Activity for Anticancer Drugs," *Proc. Am. Assoc. Cancer Res.* 26: 330, each of which is incorporated herein by reference, describe methods to aid in the determination of whether two drugs act synergistically. While synergy is not required for therapeutic benefit in accordance with the methods of the invention, synergy can improve therapeutic outcome. Two drugs can be said to possess therapeutic synergy if a combination dose regimen of the two drugs produces a significantly better tumor cell kill than the sum of the single agents at optimal or maximum tolerated doses. The "degree of synergy" can be defined as net log of tumor cell kill by the optimum combination regimen minus net log of tumor cell kill by the optimal dose of the most active single agent. Differences in cell kill of greater than ten-fold (one log) are considered conclusively indicative of therapeutic synergy.

When 2-DG is used with another anti-cancer agent, 2-DG will, at least in some embodiments, be administered prior to the initiation of therapy with the other drug or drugs and administration will typically be continued throughout the course of treatment with the other drug or drugs. In some embodiments, the drug co-administered with 2-DG will be delivered at a lower dose, and optionally for longer periods, than would be the case in the absence of 2-DG administration. Such "low dose" therapies can involve, for example, administering an anti-cancer drug, including but not limited to paclitaxel, docetaxel, doxorubicin, cisplatin, or carboplatin, at a lower than approved dose and for a longer period of time together with 2-DG administered in accordance with the methods of the present invention. These methods can be used to improve patient outcomes over currently practiced therapies by more effectively killing cancer cells or stopping cancer cell growth as well as diminishing unwanted side effects of the other therapy. In other embodiments, the other anti-cancer agent or agents will be administered at the same dose levels used when 2-DG is not co-administered. Thus, when employed in combination with 2-DG, the additional anti-cancer agent(s) are dosed using either the standard dosages employed for those agents when used without 2-DG or are less than those standard dosages. The administration of 2-DG in accordance with the methods of the invention can therefore allow the physician to treat cancer with existing (or later approved) drugs at lower doses (than currently used), thus ameliorating some or all of the toxic side effects of such drugs. The exact dosage for a given patient varies from patient to patient, depending on a number of factors including the drug combination employed, the particular disease being treated, and the condition and prior history of the patient, but can be determined using only the skill of the ordinarily skilled artisan in view of the teachings herein.

Specific dose regimens for known and approved antineoplastic agents (i.e., the recommended effective dose) are known to physicians and are given, for example, in the product descriptions found in the Physician's Desk Reference 2003, (Physicians' Desk Reference, 57th Ed) Medical Economics Company, Inc., Oradell, N.J. and/or are available from the Federal Drug Administration. Illustrative dosage regimens for certain anti-cancer drugs are also provided below.

Cancer drugs can be classified generally as alkylators, anthracyclines, antibiotics, aromatase inhibitors, bisphosphonates, cyclo-oxygenase inhibitors, estrogen receptor modulators, folate antagonists, inorganic aresenates, microtubule inhibitors, modifiers, nitrosoureas, nucleoside analogs, osteoclast inhibitors, platinum containing compounds, retinoids, topoisomerase 1 inhibitors, topoisomerase 2 inhibitors, and tyrosine kinase inhibitors. In accordance with the methods of the present invention, 2-DG can be co-administered with any anti-cancer drug from any of these classes or can be administered prior to or after treatment with any such drug or combination of such drugs. In addition, 2-DG can be administered in combination with a biologic therapy (e.g., treatment with interferons, interleukins, colony stimulating factors and monoclonal antibodies). Biologics used for treatment of cancer are known in the art and include, for example, trastuzumab (Herceptin), tositumomab and $^{131}$I Tositumomab (Bexxar), rituximab (Rituxan). In one embodiment, however, the anti-cancer drug co-administered with 2-DG is not a topoisomerase inhibitor.

Alkylators useful in the practice of the present invention include but are not limited to busulfan (Myleran, Busulfex), chlorambucil (Leukeran), ifosfamide (with or without MESNA), cyclophosphamide (Cytoxan, Neosar), glufosfamide, melphalan, L-PAM (Alkeran), dacarbazine (DTIC-Dome), and temozolamide (Temodar). In accordance with the methods of the present invention 2-DG is co-administered with an alkylator to treat cancer. In one embodiment, the cancer is chronic myelogenous leukemia, multiple myeloma, or anaplastic astrocytoma. As one example, the compound 2-bis[(2-chloroethyl)amino] tetra-hydro-2H-1,3, 2-oxazaphosphorine, 2-oxide, also commonly known as cyclophosphamide, is an alkylator used in the treatment of Stages III and IV malignant lymphomas, multiple myeloma, leukemia, mycosis fungoides, neuroblastoma, ovarian adenocarcinoma, retinoblastoma and carcinoma of the breast. Cyclophosphamide is administered for induction therapy in doses of 1500–1800 mg/m$^2$ that are administered intravenously in divided doses over a period of three to five days; for maintenance therapy, 350–550 mg/M$^2$ are administered every 7–10 days, or 110–185 mg/m$^2$ are administered intravenously twice weekly. In accordance with the methods of the invention, 2-DG is co-administered with cyclosphosphamide administered at such doses or at lower doses and/or for a longer duration than normal for administration of cyclosphosphamide alone.

Anthracyclines useful in the practice of the present invention include but are not limited to doxorubicin (Adriamycin, Doxil, Rubex), mitoxantrone (Novantrone), idarubicin (Idamycin), valrubicin (Valstar), and epirubicin (Ellence). In accordance with the methods of the present invention 2-DG is co-administered with an anthracycline to treat cancer. In one embodiment, the cancer is acute nonlymphocytic leukemia, Kaposi's sarcoma, prostate cancer, bladder cancer, metastatic carcinoma of the ovary, and breast cancer. As one example the compound (8S,10S)-10-[(3-Amino-2,3,6-trideoxy-.alpha.-L-lyxo-hexopyranosyl)oxy]-8-glycoloyl-7, 8,9,10-tetrahydro-6,8,11-trihydroxy-1-methoxy-5,12-naphthacenedione, more commonly known as doxorubicin, is a cytotoxic anthracycline antibiotic isolated from cultures of *Streptomyces peucetius var. caesius*. Doxorubicin has been used successfully to produce regression in disseminated neoplastic conditions such as acute lymphoblastic leukemia, acute myeloblastic leukemia, Wilm's tumor, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma. Doxorubicin is typically administered in a dose in the range of 30–75 mg/m$^2$ as a single intravenous injection administered at 21-day intervals; weekly intravenous injection at doses of 20 mg/m$^2$; or 30 mg/m$^2$ doses on each of three successive days repeated every four weeks. In accordance with the methods of the invention, 2-DG is co-administered starting prior to and continuing after the administration of doxorubicin at such doses (or at lower doses).

Antibiotics useful in the practice of the present invention include but are not limited to dactinomycin, actinomycin D (Cosmegen), bleomycin (Blenoxane), daunorubicin, and daunomycin (Cerubidine, DanuoXome). In accordance with the methods of the present invention 2-DG is co-administered with an antibiotic to treat cancer. In one embodiment, the cancer is a cancer selected from the group consisting of acute lymphocytic leukemia, other leukemias, and Kaposi's sarcoma.

Aromatase inhibitors useful in the practice of the present invention include but are not limited to anastrozole (Arimidex) and letroazole (Femara). In accordance with the methods of the present invention 2-DG is co-administered with an aromatase inhibitor to treat cancer. In one embodiment, the cancer is breast cancer.

Bisphosphonate inhibitors useful in the practice of the present invention include but are not limited to zoledronate (Zometa). In accordance with the methods of the present invention 2-DG is co-administered with a biphosphonate inhibitor to treat cancer. In one embodiment, the cancer is a cancer selected from the group consisting of multiple myeloma, bone metastases from solid tumors, or prostate cancer.

Cyclo-oxygenase inhibitors useful in the practice of the present invention include but are not limited to celecoxib (Celebrex). In accordance with the methods of the present invention 2-DG is co-administered with a cyclo-oxygenase inhibitor to treat cancer. In one embodiment, the cancer is colon cancer or a pre-cancerous condition known as familial adenomatous polyposis.

Estrogen receptor modulators useful in the practice of the present invention include but are not limited to tamoxifen (Nolvadex) and fulvestrant (Faslodex). In accordance with the methods of the present invention 2-DG is co-administered with an estrogen receptor modulator to treat cancer. In one embodiment, the cancer is breast cancer or the treatment is administered to prevent the occurrence or reoccurrence of breast cancer.

Folate antagonists useful in the practice of the present invention include but are not limited to methotrexate and tremetrexate. In accordance with the methods of the present invention 2-DG is co-administered with a folate antagonist to treat cancer. In one embodiment, the cancer is osteosarcoma. As one example, the compound N-[4-[[(2,4-diamino-6-pteridinyl)methyl methylamino]benzoyl]-L-glutamic acid, commonly known as methotrexate, is an antifolate drug that has been used in the treatment of gestational choriocarcinoma and in the treatment of patients with chorioadenoma destruens and hydatiform mole. It is also useful in the treatment of advanced stages of malignant lymphoma and in the treatment of advanced cases of mycosis fungoides. Methotrexate is administered as follows. For choriocarcinoma, intramuscular injections of doses of 15 to 30 mg are administered daily for a five-day course, such courses repeated as needed with rest period of one or more weeks interposed between courses of therapy. For leukemias, twice weekly intramuscular injections are administered in doses of 30 mg/m$^2$. For mycosis fungoides, weekly intramuscular injections of doses of 50 mg or, alternatively, of 25 mg are administered twice weekly. In accordance with the methods of the invention, 2-DG is co-administered with methotrexate administered at such doses (or at lower doses). 5-Methyl-6-[[(3,4,5-trimethoxyphenyl)-amino]methyl]-2,4-quinazolinediamine (commonly known as trimetrexate) is another antifolate drug that can be co-administered with 2-DG.

Inorganic arsenates useful in the practice of the present invention include but are not limited to arsenic trioxide (Trisenox). In accordance with the methods of the present invention 2-DG is co-administered with an inorganic arsenate to treat cancer. In one embodiment, the cancer is refractory acute promyelocytic leukemia (APL).

Microtubule inhibitors (as used herein, a "microtubule inhibitor" is any agent that interferes with the assembly or disassembly of microtubules) useful in the practice of the present invention include but are not limited to vincristine (Oncovin), vinblastine (Velban), paclitaxel (Taxol, Paxene), vinorelbine (Navelbine), docetaxel (Taxotere), epothilone B or D or a derivative of either, and discodermolide or its derivatives. In accordance with the methods of the present invention 2-DG is co-administered with a microtubule inhibitor to treat cancer. In one embodiment, the cancer is ovarian cancer, breast cancer, non-small cell lung cancer, Kaposi's sarcoma, and metastatic cancer of breast or ovary origin. As one example, the compound 22-oxo-vincaleukoblastine, also commonly known as vincristine, is an alkaloid obtained from the common periwinkle plant (Vinca rosea, Linn.) and is useful in the treatment of acute leukemia. It has also been shown to be useful in combination with other oncolytic agents in the treatment of Hodgkin's disease, lymphosarcoma, reticulum-cell sarcoma, rhabdomyosarcoma, neuroblastoma, and Wilm's tumor. Vincristine is administered in weekly intravenous doses of 2 mg/m$^2$ for children and 1.4 mg/m$^2$ for adults. In accordance with the methods of the invention, 2-DG is co-administered with vincristine administered at such doses. In one embodiment, 2-DG is not administered prior to treatment with a microtubule inhibitor, such as a taxane, but rather, administration of 2-DG is administered simultaneously with or within a few days to a week after initiation of treatment with a microtubule inhibitor.

Modifiers useful in the practice of the present invention include but are not limited to Leucovorin (Wellcovorin), which is used with other drugs such as 5-fluorouracil to treat colorectal cancer. In accordance with the methods of the present invention 2-DG is co-administered with a modifier and another anti-cancer agent to treat cancer. In one embodiment, the cancer is colon cancer. In one embodiment, the modifier is a compound that increases the ability of a cell to take up glucose, including but not limited to the compound N-hydroxyurea. N-hydroxyurea has been reported to enhance the ability of a cell to take up 2-deoxyglucose (see the reference Smith et al., 1999, Cancer Letters 141: 85, incorporated herein by reference), and administration of N-hydroxyurea at levels reported to increase 2-DG uptake or to treat leukemia together with administration of 2-DG as described herein is one embodiment of the therapeutic methods provided by the invention. In another such embodiment, 2-DG is co-administered with nitric oxide or a nitric oxide precursor, such as an organic nitrite or a spermineNONOate, to treat cancer, as the latter compounds stimulate the uptake of glucose and so stimulate the uptake of 2-DG.

Nitrosoureas useful in the practice of the present invention include but are not limited to procarbazine (Matulane), lomustine, CCNU (CeeBU), carmustine (BCNU, BiCNU, Gliadel Wafer), and estramustine (Emcyt). In accordance with the methods of the present invention 2-DG is co-administered with a nitrosourea to treat cancer. In one embodiment, the cancer is prostate cancer or glioblastoma, including recurrent glioblastoma multiforme.

Nucleoside analogs useful in the practice of the present invention include but are not limited to mercaptopurine, 6-MP (Purinethol), fluorouracil, 5-FU (Adrucil), thioguanine, 6-TG (Thioguanine), hydroxyurea (Hydrea), cytarabine (Cytosar-U, DepoCyt), floxuridine (FUDR), fludarabine (Fludara), pentostatin (Nipent), cladribine (Leustatin, 2-CdA), gemcitabine (Gemzar), and capecitabine (Xeloda). In accordance with the methods of the present invention 2-DG is co-administered with a nucleoside analog to treat cancer. In one embodiment, the cancer is B-cell lymphocytic leukemia (CLL), hairy cell leukemia, adenocarcinoma of the pancreas, metastatic breast cancer, non-small cell lung cancer, or metastatic colorectal carcinoma. As one example, the compound 5-fluoro-2,4(1H,3H)-pyrimidinedione, also commonly known as 5-fluorouracil, is an antimetabolite nucleoside analog effective in the palliative management of carcinoma of the colon, rectum, breast, stomach, and pancreas in patients who are considered incurable by surgical or other means. 5-Fluorouracil is administered in initial therapy in doses of 12 mg/m given intravenously once daily for 4 successive days with the daily dose not exceeding 800 mg. If no toxicity is observed at any time during the course of the therapy, 6 mg/kg are given intravenously on the 6th, 8th, 10th, and 12th days. No therapy is given on the 5th, 7th, 9th, or 11th days. In poor risk patients or those who are not in an adequate nutritional state, a daily dose of 6 mg/kg is administered for three days, with the daily dose not exceeding 400 mg. If no toxicity is observed at any time during the treatment, 3 mg/kg may be given on the 5th, 7th, and 9th days. No therapy is given on the 4th, 6th, or 8th days. A sequence of injections on either schedule constitutes a course of therapy. In accordance with the methods of the invention, 2-DG is co-administered with 5-FU administered at such doses or with the prodrug form Xeloda with correspondingly adjusted doses. As another example, the compound 2-amino-1,7-dihydro-6H-purine-6-thione, also commonly known as 6-thioguanine, is a nucleoside analog effective in the therapy of acute non-pymphocytic leukemias. 6-Thioguanine is orally administered in doses of about 2 mg/kg of body weight per day. The total daily dose may be given at one time. If after four weeks of dosage at this level there is no improvement, the dosage may be cautiously increased to 3 mg/kg/day. In accordance with the methods of the invention, 2-DG is co-administered with 6-TG administered at such doses (or at lower doses).

Osteoclast inhibitors useful in the practice of the present invention include but are not limited to pamidronate (Aredia). In accordance with the methods of the present invention 2-DG is co-administered with an osteoclast inhibitor to treat cancer. In one embodiment, the cancer is osteolytic bone metastases of breast cancer, and one or more additional anti-cancer agents are also co-administered with 2-DG.

Platinum compounds useful in the practice of the present invention include but are not limited to cisplatin (Platinol) and carboplatin (Paraplatin). In accordance with the methods of the present invention 2-DG is co-administered with a platinum compound to treat cancer. In one embodiment, the cancer is metastatic testicular cancer, metastatic ovarian cancer, ovarian carcinoma, and transitional cell bladder cancer. As one example, the compound cis-Diaminedichloroplatinum (II), commonly known as cisplatin, is useful in the palliative treatment of metastatic testicular and ovarian tumors, and for the treatment of transitional cell bladder cancer which is not amenable to surgery or radiotherapy. Cisplatin, when used for advanced bladder cancer, is administered in intravenous injections of doses of 50–70 mg/m$^2$ once every three to four weeks. In accordance with the methods of the present invention, 2-DG is co-administered with cisplatin administered at these doses (or at lower doses). One or more additional anti-cancer agents can be co-administered with the platinum compound and 2-DG. As one example, Platinol, Blenoxane, and Velbam may be co-administered with 2-DG. As another example, Platinol and Adriamycin may be co-administered with 2-DG.

Retinoids useful in the practice of the present invention include but are not limited to tretinoin, ATRA (Vesanoid), alitretinoin (Panretin), and bexarotene (Targretin). In accordance with the methods of the present invention 2-DG is co-administered with a retinoid to treat cancer. In one embodiment, the cancer is a cancer selected from the group consisting of APL, Kaposi's sarcoma, and T-cell lymphoma.

Topoisomerase 1 inhibitors useful in the practice of the present invention include but are not limited to topotecan (Hycamtin) and irinotecan (Camptostar). In accordance with the methods of the present invention 2-DG is co-administered with a topoisomerase 1 inhibitor to treat cancer. In one embodiment, the cancer is metastatic carcinoma of the ovary, colon, or rectum, or small cell lung cancer. As noted above, however, in one embodiment of the present invention, administration of 2-DG either precedes or follows, or both, administration of a topoisomerase 1 inhibitor but is not administered concurrently therewith.

Topoisomerase 2 inhibitors useful in the practice of the present invention include but are not limited to etoposide, VP-16 (Vepesid), teniposide, VM-26 (Vumon), and etoposide phosphate (Etopophos). In accordance with the methods of the present invention 2-DG is co-administered with a topoisomerase 2 inhibitor to treat cancer. In one embodiment, the cancer is a cancer selected from the group consisting of refractory testicular tumors, refractory acute lymphoblastic leukemia (ALL), and small cell lung cancer. As noted above, however, in one embodiment of the present invention, administration of 2-DG either precedes or follows, or both, administration of a topoisomerase 2 inhibitor but is not administered concurrently therewith.

Tyrosine kinase inhibitors useful in the practice of the present invention include but are not limited to imatinib (Gleevec). In accordance with the methods of the present invention 2-DG is co-administered with a tyrosine kinase inhibitor to treat cancer. In one embodiment, the cancer is CML or a metastatic or unresectable malignant gastrointestinal stromal tumor.

Thus, the present invention provides methods of treating cancer in which 2-DG or a pharmaceutically acceptable salt thereof and one or more additional anti-cancer agents are administered to a patient. Specific embodiments of such other anti-cancer agents include without limitation 5-methyl-6-[[(3,4,5-trimethoxyphenyl)amino]-methyl]-2,4-quinazolinediamine or a pharmaceutically acceptable salt thereof, (8S,10S)-10-(3-amino-2,3,6-trideoxy-alpha-L-lyxo-hexopyranosyl)oxy]-8-glycoloyl-7,8,9,10-tetrahydro-6,8,11-trihydroxy-1-methoxy-5,12-naphthacenedione or a pharmaceutically acceptable salt thereof; 5-fluoro-2,4(1H,3H)-pyrimidinedione or a pharmaceutically acceptable salt thereof, 2-amino-1,7-dihydro-6H-purine-6-thione or a pharmaceutically acceptable salt thereof, 22-oxo-vincaleukoblastine or a pharmaceutically acceptable salt thereof; 2-bis [(2-chloroethyl)amino]tetrahydro-2H-1,3,2-oxazaphosphorine, 2-oxide, or a pharmaceutically acceptable salt thereof; N-[4-[[(2,4-diamino-6-pteridinyl) methyl]-methylamino]benzoyl]-L-glutamic acid, or a pharmaceutically acceptable salt thereof; or cis-diamminedichloroplatinum (II). The methods of the present invention are generally applicable to all cancers but have particularly significant therapeutic benefit in the treatment of solid tumors, which are characterized by extensive regions of hypoxic tissue. Particular cancers that can be treated with the methods of the present invention are discussed in the following section.

Co-administration with Metabolic Inhibitors and Other Agents

Other agents that can be used in combination with 2-DG to treat cancer include glycolytic inhibitors, inhibitors of NADH/NADPH formation, and ribose-5-phosphate synthesis inhibitors, agents that increase glucose transport (as such agents, which include the taxanes, also increase 2-DG transport), flavopiridol, bryostatin, 7-hydroxystaurosporine, carboxyamide-triazole, KRN5500, spicamycin, rapamycin, non-antibiotic tetracyclines, COL-3, quinocarmycin, DX-52-1, rebeccamycin, bizelesin, dolastin 10, Rhizoxin, cryptophycin, eleutherobin, and analogs and derivatives of the foregoing compounds. The anti-cancer effect of 2-DG combination therapy can also be enhanced by the co-administration of a fatty acid oxidation inhibitor including but not limited to Ranolazine. In one embodiment, 2-DG is administered with an inhibitor of fatty acid oxidation and another anti-cancer agent, such as a cytotoxic agent, to treat cancer.

2-DG is a metabolic inhibitor and can, in accordance with the methods of the invention, be used in combination with other metabolic inhibitors and optionally with other cytotoxic or anti-cancer agents, to treat cancer. As used herein, a "metabolic inhibitor" is any compound that inhibits glycolysis (for example and without limitation by inhibiting glucose transport or inhibiting hexokinase) and/or mitochondrial function. Lonidamine, also known as Doridamina™ (ACRAF) and its analogs are metabolic inhibitors and described in U.S. Pat. Nos. 3,895,026 and 6,001,865, incorporated herein by reference. Other glycolytic inhibitors, mitochondrial function inhibitors, mitochondrial poisons, and hexokinase inhibitors useful in the methods of the present invention are described in PCT patent publication WO 01/82926 and U.S. patent application Ser. No. 09/561,720, filed 1 May 2000, now U.S. Pat. No. 6,670,330, U.S. Pat. Nos. 6,218,435; 5,824,665; 5,652,273; and 5,643,883; and U.S. patent application publication Nos. 20030072814; 20020077300; and 20020035071; each of the foregoing patent publications and patent application is incorporated herein by reference. In one embodiment, the present invention provides a method for treating cancer in a patient by administering to the patient a therapeutically effective dose of 2-DG in combination with another metabolic inhibitor.

Patient Assessment for 2-DG Treatment

In a related aspect, the present invention provides methods for treating cancer that involve a preliminary assessment of the cancer patient to determine the degree of susceptibility of the patient's cancer to 2-DG mediated drug therapy. In one aspect, this assessment evaluates the hypoxic state of the tumor, because in general the more hypoxic the tumor the more susceptible the tumor to treatment with 2-DG therapy, or the energy state of the tumor, because the lower the ATP concentration in a cancer cell, the more susceptible that cell is to treatment with 2-DG therapy. Thus, in one embodiment, the patient's tumor is probed with an oxygen sensor to determine the hypoxic state of the tumor. In one embodiment, HIF-1alpha expression in the cancer cells in the patient is examined, as increased HIF-1alpha expression correlates with increased hypoxia. In one embodiment, the cancer cells in the patient are evaluated for the level of glucose utilization or the level of glucose transporters, as increased glucose utilization and increased glucose transport indicate increased susceptibility to treatment with 2-DG. In one embodiment, the cancer cells of the patient are evaluated for ATP concentration or production, as low ATP levels indicate increased susceptibility to 2-DG mediated therapy. In one embodiment, VEGF expression is measured or otherwise determined in the patient's cancer cells, as increased VEGF expression indicates increased susceptibility to 2-DG mediated therapy.

In one embodiment, the patient's cancer cells are tested for the presence of cancer-related or cancer-causing mutations, such as p53 mutations, as such mutations often arise in the hypoxic areas of tumors and so are indicative of a tumor highly susceptible to 2-DG mediated therapy. In one embodiment, the patient's cancer is assessed for drug resistance, as 2-DG mediated therapy can render a multiple-drug-resistant cell sensitive to one or more drugs to which the cell is resistant in the absence of 2-DG.

In a first embodiment of this aspect of the invention, cancers identified by particular protein or genetic markers can be treated using 2-DG alone or in combination with another anti-cancer agent. Such markers have been identified above (HIF1a expression, VEGF expression, glucose utilization, glucose transporter level, and the like). For purposes of additional illustration, 2-DG is administered in accordance with the methods of the invention to a tumor determined to have a low level of glucose-6-phosphatase (G6Pase) activity; in another embodiment, the invention provides a diagnostic method for identifying a tumor highly susceptible to treatment with 2-DG, which method comprises obtaining a biopsy of the tumor and assaying that biopsy for glucose-6-phosphatase activity to determine whether the activity assayed is less than or equal to that of corresponding normal tissue. If the assay indicates that the G6Pase activity is less than or equal to that of corresponding normal tissue, then the tumor is highly susceptible to treatment with 2-DG in accordance with the methods of the present invention. 2-DG is believed to exert its therapeutic effect at least in part as a result of phosphorylation (creating 2-DG-6-phosphate) and accumulation of that phosphorylated product in the target cell. G6Pase removes that phosphate, allowing 2-DG to diffuse from the target cell; thus, low levels of G6Pase increase the tumor's susceptibility to 2-DG-mediated therapy.

Treating Particular Cancers

The methods and compositions of the invention may be used to treat any cancer, whether malignant or benign. In one important embodiment, the invention provides methods of treating particular types of malignant cancer, including but not limited to non-small cell lung cancer, head and neck cancers, prostate cancer, colon cancer, and breast cancer in humans and other mammals. These methods comprise administering a therapeutically effective amount of 2-DG or a pharmaceutically acceptable salt thereof either alone or in combination with an antineoplastically effective amount of one or more additional anti-cancer compounds.

The methods and compositions of the present invention can be used to treat common cancers such as bladder cancer, colorectal cancer, endometrial cancer, leukemia, lung cancer, lymphoma, melanoma, and ovarian cancer, as well as less common cancers, including but not limited to acute lymphocytic leukemia, adult acute myeloid leukemia, adult non-Hodgkin's lymphoma, brain tumors, cervical cancers, childhood cancers, childhood sarcoma, chronic lymphocytic leukemia, chronic myeloid leukemia, esophageal cancer, hairy cell leukemia, kidney cancer, renal cell carcinoma, liver cancer, multiple myeloma, neuroblastoma, oral cancer, pancreatic cancer, primary central nervous system lymphoma, skin cancer, and small-cell lung cancer. In one embodiment, 2-DG is administered in combination with Rituxan to treat lymphoma. In one embodiment, 2-DG is administered in combination with Avastin to treat renal cell carcinoma. Childhood cancers amenable to treatment by the methods, and with the compositions, of the present invention include, but are not limited to, brain stem glioma, cerebellar astrocytoma, cerebral astrocytoma, ependymoma, Ewing's sarcoma and family of tumors, germ cell tumor—extracranial, Hodgkin's disease, ALL, AML, liver cancer, medulloblastoma, neuroblastoma, non-Hodgkin's lymphoma, osteosarcoma, malignant fibrous histiocytoma of bone, retinoblastoma, rhabdomyosarcoma, soft tissue sarcoma, supratentorial primitive neuroectodermal and pineal tumors, unusual childhood cancers, visual pathway and hypothalamic glioma, and Wilms's tumor and other childhood kidney tumors.

The methods and compositions of the present invention can also be used to treat cancers that have originated in or metastasized to the bone, brain, breast, digestive and gastrointestinal systems, endocrine system, eye, genitourinary tract, germ cells, gynecological system, head and neck, hematologic system, blood, lung, respiratory system, thorax, musculoskeletal system, and skin.

In one preferred embodiment of the invention, 2-DG is administered to treat non-small-cell lung cancer (NSCLC). NSCLC is currently treated by radiation therapy, surgery, and/or chemotherapy. Simultaneous administration of 2-DG as described herein can improve treatment outcomes for all current therapies. Current treatment regimens for non-small-cell lung cancer include without limitation administration of Gemcitabine (Eli Lilly, difluorodeoxy-cytidine), vinorelbine, paclitaxel, docetaxel, cisplatin, carboplatin, or Irinotecan (camptothecin-11) as single agents; and administration of etoposide and cisplatin, Vindesine (deacetyl vinblastine carboxamide) and cisplatin, paclitaxel and carboplatin, Gemcitabine and carboplatin, docetaxel and cisplatin, vinorelbine and cisplatin, or Irinotecan and cisplatin in combination therapies. See Bunn, 15 Sep. 2002, *J. Clin. Onc.* 20(18s): 23–33, incorporated herein by reference. In accordance with the methods of the present invention, 2-DG can be co-administered in such therapeutic regimens to improve patient outcomes. For example and without limitation, co-administration of 2-DG as described herein can improve the following chemotherapies for NSCLC:

(i) administration of cisplatin in the range of 6–30 mg/m$^2$/wk by IV;

(ii) administration of cisplatin at 100 mg/m$^2$ by IV over 30–60 minutes on days 1 and 29 and vinblastine at 5 mg/m$^2$/wk by IV for 5 weeks beginning on day 1 with cisplatin;

(iii) MACC therapy, which includes 2 cycles of treatment with methotrexate at 40 mg/m$^2$ by IV on day 1 every 28 days, doxorubicin at 40 mg/m$^2$ by IV on day 1 every 28 days, cyclophosphamide at 400 mg/m$^2$ by IV on day 1 every 28 days, and lomustine at 30 mg/m$^2$ orally on day 1 every 28 days, followed by radiation followed by 2 more cycles of chemotherapy;

(iv) VCPC therapy, which includes 3 cycles of treatment with cisplatin at 100 mg/m$^2$ on day 2 every month, vindecine at 1.5 mg/m$^2$ by IV on days 1 and 2 every month, cyclophosphamide at 200 mg/m$^2$ on days 2–4 every month, and lomustine at 50 mg/m$^2$ on day 2 and 25 on day 3 every month, followed by radiation followed by 3 more cycles of chemotherapy;

(v) administration of cisplatin at 50 mg/m$^2$ by IV on days 1, 8, 29, and 36, and etoposide at 50 mg/m$^2$ by IV on days 1 to 5, 29, and 33;

(vi) administration of cisplatin at 50 mg/m$^2$ by IV over 1 hour every 21 days, mitomycin C at 6 mg/m$^2$ by IV every 21 days, and ifosfamide at 3 mg/m$^2$ by IV over 3 hours every 21 days, for 3 cycles;

(vii) administration of mitomycin C at 10 mg/m$^2$ by IV over 5–15 minutes on day 1 every 28 days, vinblastin at 6 mg/m$^2$ by IV on day 1 every 28 days, and cisplatin at 60 mg/m$^2$ by IV on over 2 hours on day 1 every 28 days;

(viii) administration of cisplatin at 100 mg/m$^2$ by IV on day 1 every 28 days and vinorelbine at 25 mg/m$^2$/wk by IV for 6 to 10 cycles or vinorelbine at 30 Mg/m$^2$/wk by IV over 20 minutes and cisplatin at 120 mg/m$^2$ by IV over 1 hour on day 1 and 29 every 6 weeks for at least 10 weeks;

(ix) administration of cisplatin at 75 mg/m$^2$ by IV over 1 hour on day 2 every 21 days and paclitaxel at 135 mg/m$^2$ by IV as a 24-hour infusion starting on day 1 every 21 days;

(x) administration of docetaxel at 75 mg/m$^2$ ever 21 days and cisplatin at 75 mg/m$^2$/wk every 21 days;

(xi) administration of gemcitabine at 1,000 mg/m$^2$ by IV over 30 to 60 minutes on days 1, 8, and 15 every 28 days and cisplatin at 100 mg/m$^2$ by IV over 30 to 120 minutes on day 1 every 28 days after the gemcitabine dose, for up 6 cycles;

(xii) administration of paclitaxel at 225 mg/m$^2$ by IV over 3 hours on day 1 every 21 days, and carboplatin by IV area under the curve of 6 on day 1 every 21 days, for 6 to 10 cycles;

(xiii) administration of paclitaxel at 200 mg/m$^2$ by IV over 3 hours on day 1 every 21 days and gemcitabine at 1,000 mg/m$^2$ IV 30 minutes on days 1 and 8 every 21 daays, for up to 6 cycles.

As shown in the examples below, continuous administration of 2-DG in combination with cisplatin is remarkably effective in stopping the growth of non-small-cell lung cancer tumors in mouse xenografts, and in a preferred embodiment, the present invention provides a method for treating NSLC that comprises administering 2-DG as described herein in combination with cisplatin.

In another preferred embodiment of the invention, 2-DG is administered to treat prostate cancer. In one embodiment, 2-DG is administered with prednisone to treat prostate cancer. The present invention also provides pharmaceutical formulations comprising prednisone admixed with 2-DG in amounts effective for the treatment of prostate cancer and suitable for oral administration. In another embodiment, 2-DG is administered with prednisone and mitoxanthrone for the treatment of prostate cancer. In another embodiment, 2-DG is administered with Taxotere™ (Aventis, docetaxel) for the treatment of prostate cancer.

In another preferred embodiment of the invention, 2-DG is administered to treat colorectal cancer or metastatic colorectal cancer. Colon or colorectal cancer is currently treated by radiation therapy, surgery, and/or chemotherapy. Simultaneous administration of 2-DG as described herein can improve treatment outcomes for all current therapies. For example and without limitation, co-administration of 2-DG as described herein can improve the following chemotherapies for colon cancer:

(i) administration of fluorouracil (5-FU) at 2,600 mg/m$^2$ by IV continuous infusion over 24 hours every week or a 400 mg/m$^2$ bolus and 600 mg/m$^2$ by 22 hour IV infusion on days 1 and 2 every 2 weeks;

(ii) administration of 5-FU at 500 milligrams per square meter daily and leucovorin at 500 milligrams per square meter daily, both administered every seventh day for 6 weeks out of every 8 weeks for 1 year (the NSABP regimen);

(iii) administration of 5-FU at 425 milligrams per square meter daily and leucovorin at 20 milligrams per square meter daily for 5 days repeated every 4 to 5 weeks for 6 months of chemotherapy (the NCCTG regimen);

(iv) administration of 5-FU at 370 to 400 milligrams per square meter daily and leucovorin at 200 milligrams per square meter daily, for 5 days every 28 days for 6 cycles;

(v) administration of fluorouracil plus levamisole for 12 months;

(vi) administration of fluorouracil plus levamisole plus leucovorin for 6 months;

(vii) administration of 5-FU at 600 mg/m$^2$ by IV bolus every week and leucovorin at 125 mg/m$^2$ orally and hourly for the preceding 4 hours every week;

(viii) administration of 5-FU at 600 mg/m$^2$ by IV bolus every week and leucovorin at 600 mg/m$^2$ by IV every week;

(ix) administration of fluorouracil at 400–425 mg/m$^2$ IV bolus daily for five consecutive days every four weeks and leucovorin at 20 mg mg/m$^2$ by IV bolus daily for five consecutive days every four weeks;

(x) administration of N-phosphonoacetyl-l-aspartic acid at 250 mg/m$^2$ by IV continuous infusion over 24 hours on day 1 every week and 5-FU at 2,600 mg/m$^2$ by IV continuous infusion over 24 hours on day 2 every week;

(xi) administration of 5-FU at 750 mg/m$^2$/d by IV by continuous infusion for 5 days, then 750 mg/m$^2$ weekly, and recombinant interferon alfa-2a at 9 million units subcutaneously three times weekly;

(xii) administration of irinotecan at 300–350 mg/m$^2$ over a 90 min intravenous infusion every 3 weeks or 125 mg/m$^2$ over a 90 min intravenous infusion every week for 4 weeks every 6 weeks;

(xiii) administration of irinotecan at 80 mg/m$^2$ every week and fluorouracil at 2,300 Mg/m$^2$ by 24 hour IV infusion every week or irinotecan at 180 mg/m$^2$ on day 1 every 2 weeks and fluorouracil at 400 mg/m$^2$ bolus and 600 mg/m$^2$ by 22 hour IV infusion on days 1 and 2 every 2 weeks;

(xiv) administration of irinotecan at 125 mg/m$^2$ IV every week for four weeks every six weeks, fluorouracil at 500 mg/m$^2$ by IV bolus every week for four weeks every six weeks, and leucovorin at 20 mg/m$^2$ IV bolus every week for four weeks every six weeks.

(xv) administration of the thymidylate synthase inhibitor raltitrexed at 3 mg/m$^2$ once every 3 weeks;

(xvi) administration of fluoropyrimidine carbamate capecitabine at 1,250 mg/m$^2$ orally twice daily in 3-week cycles (2 weeks of treatment followed by a 1-week rest period); and (xvii) administration of Oxaliplatin alone Oxaliplatin plus 5-FU plus leucovorin. In addition, Avastin™ (Genentech, Bevacizumab) and other anti-angiogenic agents have shown remarkable promise in combination with standard chemotherapies for treating colon cancer, and in an important embodiment of this invention, 2-DG is administered in combination with Avastin, and optionally other chemotherapeutic agents, including but not limited to those discussed above, to treat colon cancer. Likewise cetuximab (Erbitux®) has shown remarkable promise in combination with standard chemotherapies for treating colon cancer, and in an important embodiment of this invention, 2-DG is administered in combination with Erbitux, and optionally other chemotherapeutic agents, including but not limited to those discussed above, to treat colorectal cancer or metastatic colorectal cancer. In another embodiment, 2-DG is administered with Erbitux and Ironotecan to treat colorectal cancer or metastatic colorectal cancer.

In another preferred embodiment of the invention, 2-DG is administered to treat breast cancer. Breast cancer is commonly treated by various combinations of surgery, radiation therapy, chemotherapy, and hormone therapy. Prognosis and selection of therapy may be influenced by the age and menopausal status of the patient, stage of the disease, histologic and nuclear grade of the primary tumor, estrogen-receptor (ER) and progesterone-receptor (PR) status, measures of proliferative capacity, and HER2/neu gene amplification.

The primary tumors of stage I, II, and IIIA breast cancer are usually surgically removed by breast-conserving surgery plus radiation therapy or mastectomy with or without breast reconstruction. Radiation therapy as part of breast-conserving local therapy consists of postoperative external-beam radiation to the entire breast with median absorbed doses in the target volume of 45 Gy to 50 Gy, given in 1.8 Gy to 2.5 Gy daily fractions over an up to 5½ week period. Shorter hypofractionation schemes achieve comparable results. Radiation is delivered to the chest wall, including the surgical scar and regional lymph nodes (i.e., supraclavicular, infraclavicular, and axillary nodes as well as internal mammary nodes in the four upper intercostal spaces). A further radiation boost, delivered by external-beam radiation or by using interstitial radioactive implant, is commonly given to the tumor bed. In patients that are at high risk for local-regional recurrence after mastectomy (patients with more than four axillary node-positive tumors or extranodal involvement) the chest wall and regional lymph nodes are further irradiated. Delaying radiation therapy for several months after breast-conserving surgery until the completion of adjuvant chemotherapy appears safe and may be preferable for patients at high risk of distant dissemination.

Local-regional recurrence and overall survival at 10 years in node-negative and node-positive patients are improved by combining surgery and radiation therapy with hormone therapy or chemotherapy, and 2-DG can be administered in combination with these therapies to decrease recurrence and increase survival. Hormone therapy typically involves the administration of a daily dose of 20 to 30 mg of Tamoxifen given for 1 to 5 years starting 2–5 weeks after surgery. 2-DG can be co-administered with Tamoxifen for all or part of the time period in which Tamoxifen is administered. In addition, 2-DG can be coadministered with Tamoxifen concurrently with other treatments commonly used with or following Tamoxifen administration (chemotherapy, ovarian ablation, aromatase inhibition thereapy with letrozole, anastrozole, and exemestane).

In one embodiment, 2-DG is co-administered with standard CMF therapy to treat breast cancer. CMF therapy involves the administration of 6 cycles of: 500 or 600 mg of cyclophosphamide per square meter of body-surface area given intravenously on days 1 and 8 or 100 mg per square meter given orally on days 1 through 14, in each case every 21 to 28 days (higher doses provide no benefit); 40 mg of methotrexate per square meter given intravenously on days 1 and 8 every 21 to 28 days; and 600 mg of fluorouracil per square meter given intravenously every 21 to 28 days, with the first cycle beginning two to five weeks after surgery. In one embodiment, 2-DG is administered every day during the entire period during which the 6 cycles of CMF therapy is administered. In another embodiment, 2-DG is administered for the first five or ten days of each treatment cycle.

In one embodiment, 2-DG is co-administered with standard AC and/or ACT therapy to treat breast cancer. AC therapy involves the administration of 60 mg/m$^2$ of doxorubicin given intravenously every 21 days (higher doses provide no benefit) and 600 mg/m$^2$ of cyclophosphamide given intravenously every 21 days, for 4 cycles, the first cycle beginning within 84 days after surgery. Additional benefit may be obtained by treatment with 4 cycles of paclitaxel (175 mg/m$^2$) given intravenously every 21 days (ACT therapy). In one embodiment, 2-DG is administered every day during the entire period during which the AC and/or ACT therapy is administered. In another embodiment, 2-DG is administered for the first five or ten days of each treatment cycle.

In one embodiment, 2-DG is co-administered with standard CAF therapy to treat breast cancer. CAF therapy involves the administration of 600 mg/m$^2$ of cyclophosphamide given on day 1 of 28 day cycle for 4 cycles or 400 mg/m given on day 1 and 8 of 28 day cycle; 60 mg/m$^2$ of doxorubicin given on day 1 of 28 day cycle for 4 cycles or 40 mg/m$^2$ given on day 1 of 28 day cycle; 600 mg/m$^2$ of 5-FU given on day 1 and 8 of 28 day cycle for 4 cycles or 400 mg/m$^2$ given on day 1 and 8 of 28 day cycle; for 6 cycles. In one embodiment, 2-DG is administered every day during the entire period during which the CAF therapy is administered. In another embodiment, 2-DG is administered for the first five or ten days of each treatment cycle.

In one embodiment, 2-DG is co-administered with standard FEC therapy to treat breast cancer. FEC therapy involves the administration of 75 mg/m$^2$ of cyclophosphomide given orally on days 1 through 14 or 500 mg/m$^2$ given intravenously every 21 or 28 days; 50, 60, 100 mg/m$^2$ of epirubicin given intravenously on days 1 and 8 every 21 or 28 days; 500 mg/m$^2$ of fluorouracil given intravenously on days 1 and 8 every 21 or 28 days, for 3 to 6 cycles with the first cycle beginning within 42 days after surgery. In one embodiment, 2-DG is administered every day during the entire period during which the FEC therapy is administered. In another embodiment, 2-DG is administered for the first five or ten days of each treatment cycle.

Initial treatment of stage IIIB breast cancer with anthracycline-based chemotherapy and/or taxane-based therapy is standard. As noted, the present invention provides 2-DG combination therapies using anthracyclines and taxanes. Local therapy may consist of total mastectomy with axillary lymph node dissection followed by postoperative radiation therapy to the chest wall and regional lymphatics. Subsequent systemic therapy may consist of further chemotherapy and/or hormone therapy. Treatment of stage IV metastatic breast cancer usually involves hormone therapy and/or chemotherapy with or without trastuzumab (Herceptin). In accordance with the methods of the invention, 2-DG is co-administered with Herceptin to treat stage IV metastatic breast cancer. Radiation therapy and/or surgery may be indicated for patients with limited symptomatic metastases. Hormone therapy may include administration of Tamoxifen as noted above; LHRH agonist buserelin; aromatase inhibitors anastrozole, letrozole, or exemestane; megestrol acetate; estrogens; androgens; ER down regulator fulvestrant; and raloxifen, and 2-DG can be co-administered with each of these agents in accordance with the methods of the invention.

Patients whose tumors have progressed on hormone therapy and patients with hormone receptor-negative tumors or visceral metastases are candidates for cytotoxic chemotherapy. Agents that have shown activity in metastatic breast cancer include: the anthracyclines, such as doxorubicin, epirubicin, liposomal doxorubicin, and mitoxantrone; taxanes, such as paclitaxel and Docetaxel; alkylating agents, such as cyclophosphamide; fluoropyrimidines, such as capecitabine and 5-FU; antimetabolites such as methotrexate, vinca alkaloids such as vinorelbine, vinblastine, and vincristine; platinum-containing compounds such as carboplatin and cisplatin, as well as other agents, such as gemcitabine and mitomycin C. Combination regimens include: CA: cyclophosphamide and doxorubicin; Docetaxel and doxorubicin; CAF: cyclophosphamide, doxorubicin, 5-fluorouracil; CMF: cyclophosphamide, methotrexate, 5-fluorouracil; Doxorubicin and paclitaxel given as a combination or sequentially; and docetaxel and capecitabine. In accordance with the methods of the invention, 2-DG can be co-administered with any of these agents and with any of these combinations of agents to treat recurrent or metastatic breast cancer.

Other cancer-related conditions amenable to treatment with 2-DG include ductal carcinoma in situ (DCIS) and lobular carcinoma in situ (LCIS). DCIS is a noninvasive neoplasm of ductal origin that can progress to invasive cancer. DCIS is typically treated with mastectomy or local excision by breast conserving surgery and breast irradiation. Administration of tamoxifen (20 mg daily for 5 years) has been shown to add to the efficacy of breast-conserving surgery and radiation therapy (50 Gy). Tamoxifen may also be combined with total mastectomy. LCIS is not a premalignant lesion. However, it identifies women who are at an increased risk for subsequent development of invasive breast cancer. Women with LCIS are generally subjected to diagnostic biopsy and are then carefully monitored for early signs of breast cancer. Although not yet in routine use, tamoxifen has been shown to decrease the incidence of subsequent breast cancers in LCIS patients. In accordance with the invention, 2-DG can be administered in combination with Tamoxifen or with surgery and/or radiation as a therapy for DCIS or LCIS.

Treating Diseases Other Than Cancer

2-DG administered and formulated as described herein can have therapeutic benefit for diseases and conditions other than cancer. Daily administration of 2-DG as described herein can help control weight gain, particularly if the subject is adhering to a low carbohydrate diet, such as the Adkins diet, as well as provide other benefits associated with fasting, and 2-DG can be used to treat Parkinson's as well as certain infectious diseases.

The administration of 2-DG can stimulate dopamine release in the brain. The present invention provides a method for treating Parkinson's disease and ameliorating the symptoms thereof by administering a therapeutically effective dose of 2-DG. In one embodiment of this method, the 2-DG is administered only after symptoms of Parkinson's disease appear and then only until the symptoms are ameliorated, with administration being re-initiated only when symptoms reappear. In some embodiments of the method, an amount of 2-DG in the range of 100 mg to 5 g of 2-DG per kg of patient weight per day is administered. In other embodiments, the range is 0.5 g to 4 g, or 1 to 3 g. Each daily dose can be administered in a single bolus, or the dose can be divided into smaller doses that are administered throughout the day. In one embodiment, the dose is administered orally.

While the administration of 2-DG alone is effective in the treatment of Parkinson's disease, the methods of the present invention include methods in which 2-DG is administered in combination with another drug used in the treatment or prevention of Parkinson's disease.

The present invention also provides methods for treating infectious diseases caused by anaerobes in humans and other mammals, as well as methods for killing anaerobic organisms wherever they occur, said methods comprising contacting said organisms with a lethal dose of 2-DG. Organisms like yeast, which are anaerobic, are responsible for a number of infections in humans, including but not limited to the vaginal yeast infection caused by *Candida albicans*. Anaerobes depend on glycolysis for survival, and 2-DG can be used to poison such anaerobes and thus treat the infectious diseases caused by them. In one method of the invention, 2-DG is administered as a vaginal suppository to treat a yeast infection. In another method of the invention, the 2-DG is administered with another agent used to treat yeast infections, such as, for example, clortrimazole. In another method of the invention, a dose of the other agent lower than the minimum recommended dose is administered, because 2-DG potentiates the action of the other agent.

Administration of 2-DG in the doses described herein and using the formulations described herein can also have therapeutic benefit in the treatment of inflammatory disease, including but not limited to arthritis. For treatment of a chronic inflammatory disease such as arthritis, 2-DG will typically be administered daily for the life of the patient.

Formulation and Packaging of 2-DG

A decided practical advantage of the compounds of the present invention is that the compounds can be administered in any convenient manner such as by the oral, intravenous, intramuscular, topical, or subcutaneous routes. Micronized 2-DG can also be milled and packaged in an insufflator equipped with a dosing pump for administration by insufflation.

2-DG can be orally administered, for example, with an inert diluent or with an assimilable edible carrier, or it can be enclosed in hard or soft shell gelatin capsules, or compressed into tablets, or suspended in a liquid or gel, or incorporated directly with the food of the diet. For oral therapeutic administration, 2-DG can be incorporated with excipients and used in the form of ingestible tablets, buccal tablets, troches, capsules, elixirs, suspensions, syrups, wafers, and the like. Such compositions and preparations contain enough of the active agent to deliver the therapeutically active doses described above. The tablets, troches, pills, capsules, and the like may also contain the following: a binder such as gum tragacanth, acacia, corn starch, or gelatin; excipients such as dicalcium phosphate; a disintegrating agent such as corn starch, potato starch, alginic acid, and the like; a lubricant such as magnesium stearate; a sweetening agent such as saccharin; and/or a flavoring agent such as peppermint, oil of wintergreen, or cherry flavoring. When the dosage unit form is a capsule, it can contain, in addition to materials of the above types, a liquid carrier. Various other materials can be present as coatings or to otherwise modify the physical form of the dosage unit. For instance, tablets, pills, or capsules can be coated with shellac. A syrup or elixir can contain the active compound, a sweetening agent, methyl and propylparabens as preservatives, and a flavoring such as cherry or orange flavor. Of course, any material used in preparing any dosage unit form should be pharmaceutically pure and substantially non-toxic in the amounts employed. In addition, the active compound can be incorporated into sustained-release preparations and formulations.

The present invention provides a pharmaceutically acceptable formulation of 2-DG useful in the methods of the present invention. In one embodiment, the formulation is crystalline in nature, and the 2-DG is packaged in a sachet for later decantation into a potable liquid for oral administration to the patient. In this embodiment, the liquid can be a syrup or, more conveniently, a commonly consumed liquid, such as water, fruit juice, Crystal Light™ (Kraft), or cola. Usually, the liquid used to dissolve, dilute, or suspend 2-DG in a formulation of the invention will be glucose-free. In another embodiment, the 2-DG is formulated as a tablet or pill containing 2-DG in an amount in the range of about 10 mg to about 110 g. In some embodiments, each tablet or pill contains about 100 mg to about 5 g of 2-DG. In one embodiment, each tablet or pill contains 1 g of 2-DG.

The present invention provides a pharmaceutically acceptable formulation of 2-DG useful in the treatment methods disclosed herein. The 2-DG formulations of the invention include, but are not limited to, those suitable for oral administration and for parenteral injection. For parenteral injection (e.g., intravenous, intramuscular, subcutaneous, intraperitoneal, intratumoral),2-DG is dissolved or suspended in a sterile solution suitable for injection. For parenteral administration, the 2-DG formulations of the invention can contain 2-DG admixed with one or more pharmaceutically acceptable ingredients, such as a tonicity agent (including but not limited to NaCl, mannitol, and the like), an antioxidant (including but not limited to sodium bisulfite, sodium metabisulfite, ascorbic acid, and the like), and a preservative (including but not limited to benzyl alcohol, methyl paraben, propyl paraben, a combination of methyl and propyl parabens, and the like). In one embodiment, a suitable liquid formulation of the invention comprises 2-DG at a concentration in the range of 1 to 450 mg/mL, more preferably in the range of 50 to 250 mg/mL. In one embodiment, the concentration of 2-DG is 100 mg/mL.

For oral administration, 2-DG may be administered in a form suitable for oral administration, including dosage forms of tablet, capsule, caplet, and solution (e.g., dissolved or suspended in a sterile solution for administration). For oral administration, the present invention provides both preservative-free and preservative-containing formulations. Illustrative preservatives that can be employed in the preservative-containing oral liquid formulations of the invention include, but are not limited to, benzyl alcohol (0.1–1%), methylparaben (0.05–0.5%), propylparaben (0.01–0.1%) and mixtures of methyl and propyl parabens. In one embodiment, the liquid 2-DG formulation contains 100 mg/mL of 2-DG, 0.18% methylparaben, and 0.2% propylparaben. In another formulation of the invention, the 2-DG is either a solid or amorphous or crystalline in nature, and the 2-DG is packaged in a sachet or other container for dissolution in a liquid for oral administration to the patient. In one embodiment, crystalline 2-DG is admixed with one or more preservatives to prepare a stable formulation of the invention. In another embodiment, the 2-DG is formulated as a tablet or pill containing 2-DG in the range of about 50 mg to about 5 g.

The 2-DG can also be administered parenterally or intraperitoneally For parenteral administration, the 2-DG solution can be administered by intravenous infusion, typically by diluting the drug product in Sterile Water for Injection, Bacteriostatic Water for Injection, Sodium Chloride Injection (0.45%, 0.9%), Dextrose Injection (2.5%, 5%, 10%), Lactated Ringer's Injection, and the like, provided, however, that in a preferred embodiment, the formulations of the invention are essentially free of glucose or complex sugars that contain glucose. A solution of the active compound as a free acid or pharmacologically acceptable salt can be prepared in water suitably mixed with a surfactant such as hydroxypropylcellulose. Dispersions can also be prepared in glycerol, liquid polyethylene glycols and mixtures thereof, and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and, in final form, must be fluid to the extent that easy syringability exists. It must be stable under the conditions of manufacture and storage and must be preserved against the contaminating action of microorganisms such as bacteria and fungi.

2-DG can also be administered topically, e.g., using a transdermal patch. The pharmaceutical forms suitable for topical use include oil and water emulsions and liposomal formulations, as well as lotions, creams, and ointments commonly used for topical administration of drugs. The topical formulation optionally includes one or more additional anti-cancer agents to be co-administered with the 2-DG. The carrier can be a solvent or dispersion medium containing, for example, water, ethanol, polyol, for example, glycerol, propylene glycol, and liquid polyethylene glycol, and the like, suitable mixtures thereof, and vegetable oils. The proper fluidity can be maintained, for example, by the use of a coating such as lecithin, by the maintenance of the required particle size in the case of dispersion, and by the use of surfactants. The prevention of the action of microorganisms can be brought about by various anti-bacterial and anti-fungal agents, for example, parabens, chlorobutanol, phenol, sorbic acid, thimerosal, and the like. In many cases, it will be preferable to include isotonicity agents, for example sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile filtered solution thereof.

As used herein, a "pharmaceutically acceptable carrier" includes any and all solvents, dispersion media, coatings, antibacterial and antifungal agents, isotonicity agents, absorption delaying agents, and the like. The use of such media and agents for pharmaceutical active substances is well known in the art. Except insofar as any conventional media or agent is incompatible with the active ingredient, its use in the therapeutic compositions of the invention is contemplated. Supplementary active ingredients can be incorporated into the compositions of the invention.

The present invention also provides slow release forms of 2-DG. Those of skill in the art will appreciate that the frequency of dosing of a slow-release form of 2-DG will be different from the dosing frequency described herein for non-slow-release formulations and dependent on the pharmacokinetics of the particular slow release form employed. In one embodiment, the slow release form is a pharmaceutical formulation in which the 2-DG is embedded in or coated by a material from which the 2-DG is released over an extended period of time. Examples of slow release (also called sustained-release) formulations for other drugs that can be modified in accordance with the teachings herein to be useful in the present invention are well known in the art, and are, for example, described in U.S. Pat. Nos. 5,968,551; 5,266,331; 4,970,075; 5,549,912; 5,478,577; 5,472,712; 5,356,467; 5,286,493; 6,294,195; 6,143,353; 6,143,322; 6,129,933; 6,103,261; 6,077,533; 5,958,459; and 5,672,360. Sustained-release formulations are also discussed in the scientific literature, e.g., in ORAL SUSTAINED RELEASE FORMULATIONS: DESIGN AND EVALUATION, edited by A. Yacobi and E. Halperin-Walega, Pergamon Press, 1988, which describes a variety of types of sustained-release dosage forms and drug release mechanisms, for example single unit (e.g., matrix tablets, coated tablets, capsules), multiple unit (e.g., granules, beads, micro-capsules), inert, insoluble matrix, hydrophilic gel matrix (e.g., bioadhesive, erodible, non-erodible), and ion-exchange resin sustained-release dosage forms.

The present invention also provides slow release forms of 2-DG in which an acid labile polyethylene glycol (PEG) moiety is attached to the 2-DG, preferably at the hydroxyl groups at the 4 and 6 positions. Such a slow release form can be readily synthesized by first treating PEG (polyethylene glycol) with Des Martin periodinane and reacting the resulting aldehyde 2-DG. The resulting compound is novel, having the structure shown below.

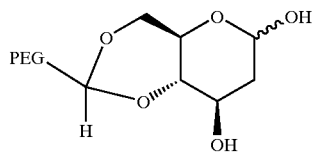

It is advantageous to formulate parenteral and other compositions in unit dosage form for ease of administration and uniformity of dosage. Unit dosage form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel unit dosage forms of the invention is dictated by and directly dependent on the patient and cancer to be treated and can vary from patient to patient and cancer to cancer, but generally, a unit dosage form contains from about 10 mg to about 20 g of 2-DG. Typical unit forms can contain about 0.35 to about 10 g of 2-DG, or from 1 to 7 g of 2-DG, or from 2 to 4 g of 2-DG.

The present invention provides a kit containing 2-DG formulated for oral delivery together with instructions for patient use detailing the drug administration procedures and schedule set forth herein. The present invention also provides (i) a transdermal delivery device containing 2-DG formulated for transdermal delivery according to the present invention; (ii) an infusion pump loaded with 2-DG suitable for use in the present methods; (iii) 2-DG in unit dosage form contained in a "compliance dispenser" designed for a specified administration schedule.

The present invention having been described in detail in the preceding sections, the following examples are provided to illustrate certain aspects of, but not to limit, the invention.

EXAMPLE 1

Growth Inhibitory Activity of 2-Deoxy-D-Glucose Against Human Non-small-cell Lung Carcinoma Cell Lines In this example, 2-deoxy-D-glucose (2-DG) was demonstrated to inhibit two cell lines obtained from human non-small cell lung carcinomas (NSCLC). The human lung tumor cell lines were MV522 and NCI-H23, both of which were derived from tumors displaying histopathology of adenocarcinoma, one of the at least three types of NSCLC. The NCI-H23 tumor cell line is available from the ATCC (Rockville, Md.), and the MV522 cell line was obtained by Dr. M. J. Kelner of the University of California. The cells were cultured in RPMI medium (Nova Tech, Grand Island, N.Y.) at 37° C. in a humidified atmosphere containing 5% $CO_2$. For passaging, cells grown in 75 cm² flasks (60–70% confluency) were washed with PBS and dislodged from the flasks with trypsin (Gibco BRL) before being passaged. Cells used for the experiments described below were centrifuged and resuspended in cell culture medium at a concentration of $10^5$ cells/mL. A 100 microliter aliquot (ten thousand cells) was plated into each well of a 96-well microtiter plate. The cells were then incubated for 24 hours at 37° C. in a humidified atmosphere containing 5% $CO_2$ prior to exposure to the 2-DG or other anti-cancer agent. Cultures were treated for 72 hours with a range of concentrations of 2-DG solubilized in cell culture medium. Docetaxel (Taxotere™, Aventis Pharmaceuticals, Inc.) solubilized in 100% DMSO and diluted 1000×to the desired concentration (0.1% DMSO final concentration), was used as a positive control. The Sulforhodamine B (SRB) assay, a dye-based method for determining cell number by virtue of SRB binding to basic amino acids of cellular macromolecules, was employed to assess the growth inhibitory activity of 2-DG. Exponentially growing cells in 100 microliters of cell culture medium were plated on Day 0 in 96-well microtiter plates at a concentration of $10^4$ cells/well. On Day 1, drugs were added to each well of the microtiter plate with the designated concentration in 100 microliter aliquots of cell culture medium and incubated at 37° C. in a humidified incubator (5% CO2/95% HEPA filtered air). After three days of treatment, adherent cells were fixed by adding 50 microliters of cold 50% trichloracetic acid to each well and incubating for one hour at 4° C. The supernatant was discarded, and plates were washed twice with de-ionized water and air-dried. One hundred microliters of SRB solution were added to each well of the plate and incubated ten minutes at room temperature. Unbound SRB stain was removed by washing twice with 1% acetic acid. The bound SRB stain was solubilized with 10 mM Tris buffer, and the optical densities read at a single wavelength of 515 nm.

$IC_{50}$ values (50% effective dose) were calculated from two different experiments, each of which involved 6 replicates for each dose tested. The data is presented as percent growth inhibition, where 0% represents the mean value in wells to which only vehicle (0.1% DMSO final concentration) was added and was calculated as follows: % Growth Inhibition= $(1-(OD_{test}/OD_{vehicle})\times 100$, where $OD_{test}$ is the optical density of the tested sample, and $OD_{vehicle}$ is the optical density of the vehicle in which each respective drug is dissolved. $IC_{50}$ values were determined using PRISM GraphPad software and were calculated using the formula: $Y=\text{Bottom}+[(\text{Top}-\text{Bottom})/(1+10^{(LogIC50-X)*HillSlope})]$, where X is the logarithm of drug concentration, and Y is the response, the variable Bottom is the Y value for the bottom plateau, Top is the Y value for the top plateau, and Log IC50 is the X value when the response is halfway between Bottom and Top. The variable HillSlope describes the steepness of the curve.

Treatment with 2-DG inhibited the growth of MV522 and NCI-H23 cells with mean IC50 values of 3.738±0.74 and 1.855±0.532 mM, respectively. Docetaxel, an FDA-approved drug for NSCLC, inhibited growth in MV522 and NCI-H23 tumor lines with mean IC50 values of 2.113±0.601 and 1.644±0.2115 nM, respectively. These results demonstrate that lung tumor cells are sensitive to 2-DG.

EXAMPLE 2

Evaluation of 2-DG as a Single Agent and in Combination with Cisplatin and Paclitaxel The efficacy of 2-deoxy-D-glucose (2-DG) was tested alone and in combination with cisplatin and compared with cisplatin alone in a tumor growth delay study in a mouse MV522 xenograft model as follows. Female nude mice (nu/nu) between 5 and 6 weeks of age and weighing approximately 20 g were obtained from Harlan, Inc. (Madison, Wis.). Animals were implanted subcutaneously by trocar with fragments of Mv522 human tumor carcinomas harvested from subcutaneously growing tumors in nude mice hosts. When the tumors were approximately 71 mg in size (11 days following inoculation), the animals were pair-matched into treatment and control groups. Each group contained 10 tumored mice. Each mouse was ear-tagged and followed individually throughout the experiment. Initial doses were given on Day 1 following pair-matching. 2-DG was administered orally (p.o.) on a 12-hour twice daily×5 to end (bid×5 to end) schedule. On Days 1–14, 2-DG was administered at doses of 50, 150, 400 and 750 mg/kg as a single agent or, in the combination regimen groups, with cisplatin. The 2-DG doses of 50, 150, and 400 mg/kg were increased to 1000, 1500, and 2000 mg/kg, respectively, on Day 15. Cisplatin was intraperitoneally (i.p.) administered starting on Day 1 at doses of 1 and 2 mg/kg on a qd×5 schedule paclitaxel was administered i.p. at 16 mg/kg on Days 1–5 to serve as the positive control. Sterile water was administered orally bid×5 to end to serve as the negative control. Mice were weighed twice weekly, and tumor measurements were obtained using calipers twice weekly, starting on Day 1. These tumor measurements were converted to mg tumor weight by the standard formula $(W^2 \times L)/2$. Each mouse was sacrificed when its tumor weight reached 1000 mg. In this test, the average day of sacrifice was determined for all groups and the tumor growth delay (TGD) for each treatment group, compared to the control group, was calculated.

In the single agent tests, the negative control group was dosed p.o. on a bid×5 to end schedule; the vehicle was sterile water. The negative control had a mean day of sacrifice of 22.4+/−1.4. Paclitaxel served as the positive control and was administered i.p. on Days 1–5 at 16 mg/kg. paclitaxel had a mean day of sacrifice of 56.8+/−4.3. This resulted in a TGD of 34.4 days with one mouse experiencing a complete regression. Animals in the paclitaxel group experienced some weight loss. On Days 4 and 15, mean weight changes were recorded at −9.9% and 2.0%, respectively. There were no toxic deaths reported in the paclitaxel group. Oral administration of 2-DG at 750 mg/kg on a bid×5 to end schedule resulted in a mean day of sacrifice of 28.9+/−3.7. 2-DG administered p.o. at 1000 mg/kg (Days 1–14 dose was 50 mg/kg) on a bid×5 to end schedule resulted in a mean day of sacrifice of 27.2+/−2.7. P.o. administration of 2-DG at 1500 mg/kg (Days 1–14 dose was 150 mg/kg) on a bid×5 to end schedule resulted in a mean day of sacrifice of 28.2+/−4.6. 2-DG administered p.o. at 2000 mg/kg (Days 1–14 dose was 400 mg/kg) on a bid×5 to end schedule resulted in a mean day of sacrifice of 29.4+/−3.1. This activity was comparable to the negative control, which had a mean day of sacrifice of 22.4+/−1.4. Animals in the 2-DG groups experienced little weight loss, and there were no toxic deaths reported in any of the 2-DG single agent groups.

For the combination regimens, the results were as follows. The negative control group was dosed p.o. on a bid×5 to end schedule. The vehicle consisted of sterile water and saline. The negative control had a mean day of sacrifice of 26.5+/−2.1. Cisplatin, administered as a single agent, served as the positive control for the study and was administered i.p. on Days 1–5 at two doses: 1 mg/kg and 2 mg/kg. Cisplatin had a mean day of sacrifice of 42.3+/−0.9 and 59.1+/−5.7, respectively, at these doses. This resulted in a TGD of 15.8 for cisplatin at 1 mg/kg and 32.6 days for cisplatin at 2 mg/kg. Two mice in the high dose cisplatin group experienced complete regressions. Animals in both cisplatin groups experienced acceptable weight loss. On Days 4 and 15, mean weight changes for 1 mg/kg cisplatin were recorded at −9% and 1.9%, respectively. On Days 4 and 15, mean weight changes for 2 mg/kg cisplatin were recorded at −13.3% and 3.2%, respectively. There were no toxic deaths reported in the cisplatin single agent groups.

Oral administration of 2-DG at 750 mg/kg on a bid×5 to end schedule in combination with cisplatin (1 mg/kg, i.p., qd×5) resulted in a mean day of sacrifice of 40.5+/−1.4. 2-DG administered p.o. at 1000 mg/kg (Days 1–14 dose was 50 mg/kg) on a bid×5 to end schedule in combination with cisplatin (1 mg/kg, i.p., qd×5) resulted in a mean day of sacrifice of 52.6+/−3.4. Oral administration of 2-DG at 1500 mg/kg (Days 1–14 dose was 150 mg/kg) on a bid×5 to end schedule in combination with cisplatin (1 mg/kg, i.p., qd×5) resulted in a mean day of sacrifice of 52.8+/−2. 2-DG administered p.o. at 2000 mg/kg (Days 1–14 dose was 400 mg/kg) on a bid×5 to end schedule in combination with cisplatin (1 mg/kg, i.p., qd×5) resulted in a mean day of sacrifice of 52+/−2.5. The activity of the 1000, 1500, and 2000 mg/kg combination regimens was superior to single-agent cisplatin (1 mg/kg, i.p., qd×5), which had a mean day of sacrifice of 42.3+/−0.9. Animals in the 2-DG/cisplatin groups experienced acceptable weight loss, and there were two toxic deaths reported in the 2-DG (2000 mg/kg)/cisplatin combination group.

Oral administration of 2-DG at 750 mg/kg on a bid×5 to end schedule in combination with cisplatin (2 mg/kg, i.p., qd×5) resulted in a mean day of sacrifice of 68.1+/−3. 2-DG administered p.o. at 1000 mg/kg (Days 1–14 dose was 50 mg/kg) on a bid×5 to end schedule in combination with cisplatin (2 mg/kg, i.p., qd×5) resulted in a mean day of sacrifice of 73+/−2.8. Oral administration of 2-DG at 1500 mg/kg (Days 1–14 dose was 150 mg/kg) on a bid×5 to end schedule in combination with cisplatin (1 mg/kg, i.p., qd×5) resulted in a mean day of sacrifice of 73.8+/−3.5. 2-DG administered p.o. at 2000 mg/kg (Days 1–14 dose was 400 mg/kg) on a bid×5 to end schedule in combination with cisplatin (1 mg/kg, i.p., qd×5) resulted in a mean day of sacrifice of 76.7+/−4.2. The activity of all combination regimens was superior to single-agent cisplatin (2 mg/kg, i.p., qd×5), which had a mean day of sacrifice of 59.1+/−5.7. Animals in the 2-DG/cisplatin groups experienced acceptable weight loss, and there was one toxic death reported in the 2-DG (1500 mg/kg)/cisplatin combination group.

The maximum tolerated dose determination for this study was conducted using female nude mice (nu/nu) between 5 and 6 weeks of age weighing approximately 20 g (Harlan, Inc., Madison, Wis.). Dosing began on Day 1. 2-DG (Ferro Pfanstiehl Laboratories, Inc. (Lot 28506A); 2-DG can also be purchased from Sigma) was dosed on a 12-hour bid×5 schedule. A 20 mL/kg dose volume was used to achieve doses of 2000, 4000, 6000, 8000, and 9000 mg/kg/dose. Individual mouse weights in grams were recorded twice weekly throughout the study. The average weight per group was calculated, and weight gain or loss was determined by comparing the current Day's average to the Day 1 average for that same group. The study was terminated on Day 21. All 5 mice died in the 8000 and 9000 mg/kg/dose groups. One mouse died in the 6000 mg/kg/dose group, which had a maximum weight loss of 5.2%. No deaths or weight loss were observed in the other two groups; 4000 mg/kg/dose was determined to be the maximum tolerated dose. Thus, the MTD for 2-DG was 4000 mg/kg/dose when dosed twice a day for 5 days (Study No. TH-PT-001 in Table I). An MTD study (TH-PT-002) was also done to compare the toxicity of a combined 2-DG/cisplatin treatment with cisplatin alone. Nontumored nude mice were treated with 2, 3, or 4 mg/kg/dose i.p. cisplatin, dosed qd on Days 6–10 with or without 2-DG dosed orally at 2000 mg/kg/dose, qd on days 1–10. No mice died during the 21 days of the study, and there was no significant difference in body weights between the mice dosed with cisplatin and 2-DG or cisplatin alone. Thus, 2-DG at 2000 mg/kg did not increase the toxicity of cisplatin at 2, 3, or 4 mg/kg (Study No. TH-PT-002).

In addition to the study of 2-DG alone and 2-DG in combination with cisplatin (Study No. TH-PT-001) reported above, additional studies were done in the nude mouse xenograft model of non-small cell lung cancer (NSCLC) using MV522 tumors, which have been shown to be chemotherapy-resistant (Kelner et al., 1995). In these additional studies (Nos. TH-PT-002 and -003), 2-DG was given orally in combination with cisplatin or paclitaxel, and the effect on the average time for tumors to reach 1000 mg was examined. All of these studies are outlined in the following table.

TABLE I

| Study Type | Study Number | 2-DG Dose Levels (mg/kg/dose) | Chemo-therapy | Chemo-therapy Dose Levels (mg/kg/dose) |
|---|---|---|---|---|
| MTD | TH-PT-001 | 0, 2000, 4000, 6000, 8000, 9000 | — | |
| TGD[a] | TH-PT-001 | 0, 750/750[b], 50/1000, 150/1500, 450/2000 | Cisplatin | 0, 1, 2 |
| TGD | TH-PT-003 | 0, 500, 1000, 2000 | Cisplatin | 1 |
| TGD | TH-PT-003 | 0, 500, 1000, 2000 | paclitaxel | 10 |
| LD50 | TH-PT-002 | 2000 | Cisplatin | 2, 3, 4 |

[a]tumor growth delay
[b]dose: days 1–15 (AM)/days 15 (PM)-end

As noted above, 2-DG as a single agent (0–2000 mg/kg/dose, twice a day) did not slow the tumor growth rate. The combination of cisplatin (1 or 2 mg/kg/dose, once a day (qd), i.p.×5 days/week, starting on Day 1 when tumors were ~70 mg) and oral 2-DG (1000–2000 mg/kg/dose, bid, to sacrifice, starting on Day 1) resulted in a significant ($P<0.05$) increase in tumor growth delay (TGD). As noted, the dose of 2-DG in this study (TH-PT-001) was significantly lower for the first 15 days (0–450 mg/kg/dose), except in the 750 mg/kg/dose group, where no increase in efficacy over chemotherapy alone was observed. All treatment regimens were well-tolerated with body weight losses for the combined therapy groups being similar to cisplatin alone.

In a second study with 2-DG and cisplatin (TH-PT-003), 2-DG dosing (0, 500, 1000, 2000, 4000 mg/kg/dose) began on Day 1, and cisplatin dosing (1 mg/kg/dose, i.p., qd×5) began on day 6. 2-DG dosing was either bid or qd to sacrifice, except for a few groups where 2-DG was dosed only on Days 1–10. No statistically significant increase in TGD was observed for any 2-DG/cisplatin dose group when compared to cisplatin treatment alone in this study. 2-DG at 2000 and 4000 mg/kg/dose in combination with cisplatin (1 mg/kg) was toxic, resulting in mortality after 17 and 8 days of dosing, respectively. Lower doses of 2-DG, or 2-DG at 2000 mg/kg/dose for only 10 days, in combination with cisplatin were well tolerated. Body weight changes for the combined treatment groups were similar to those for cisplatin alone. A comparison of these two studies with 2-DG and cisplatin shows that, in the first study, the dosing of cisplatin began on Day 1, whereas in the second study, dosing began on Day 6. The average tumor size on Days 1 and 6 were 65 mg and 200 mg, respectively, and larger tumors are typically harder to treat.

The third efficacy study (TH-PT-003) investigated the effect of paclitaxel alone or in combination with oral 2-DG on tumor growth delay. As in the second cisplatin/2-DG study, 2-DG dosing began on Day 1 (tumors ~70 mg), paclitaxel dosing began on day 6 (i.p., qd×5), and the model was a human xenograft of MV522 non-small cell lung cancer (NSCLC) in nude mice. An increase in efficacy was defined as a significant ($P<0.05$) increase in the time for the tumor to grow to 1000 mg (tumor growth delay—TGD) compared to vehicle alone or, for combination treatment groups, chemotherapy alone, as calculated using a two-tailed t-test. Female nude mice, ten per treatment arm, were implanted subcutaneously (s.c.) with trocar fragments of MV522 tumors harvested from s.c. tumors growing in nude mice hosts. Body weights and tumor measurements were taken biweekly. When tumors reached ~70 mg, treatment was started. Mice were sacrificed when their individual tumor reached ~1000 mg. All doses are reported as mg/kg/dose. Mice were treated orally, starting on day 1, with 2-DG at 500, 1000, or 2000 mg/kg/dose bid until sacrifice or 2000 or 4000 mg/kg/dose bid for 10 days. The mice were then dosed i.p. with 10 mg/kg/dose paclitaxel once a day on days 6–10. Dosing of 2-DG started when the tumors were an average size of 71 mg. Dosing with paclitaxel began when the tumors were approximately 200 mg.

The combination treatment of 2-DG bid at 2000 or 4000 mg/kg/dose and paclitaxel at 10 mg/kg/dose resulted in mortality starting on days 18 and 9, respectively, with 7 and 10 of 10 mice dying, respectively. One death per group was also observed in each of the paclitaxel alone and paclitaxel+500 mg/kg/dose 2-DG groups. The combination of paclitaxel and 2-DG at 500 or 1000 mg/kg/dose for the duration of the experiment or 2-DG at 2000 mg/kg/dose for 10 days was well tolerated with acceptable changes in body weight. Tumor growth rates for mice dosed with paclitaxel alone were similar to vehicle control. At 2-DG doses of 1000 (bid) and 2000 (bid×10) mg/kg/dose, significant ($P<0.05$) increases in TGD (11 and 10 days, respectively) were observed compared to paclitaxel alone. 2-DG at a dose of 2000 mg/kg/dose, given only on days 1–10 was more efficacious than 2-DG given at 1000 mg/kg/dose until sacrifice. 2-DG at 500 mg/kg/dose in combination with paclitaxel showed a small but insignificant increase in TGD. The addition of 2-DG to paclitaxel resulted in a dose-dependent increase in tumor growth delay which was significant ($P<0.05$) at 1000 mg/kg/dose (bid dosing, to sacrifice) and 2000 mg/kg/dose 2-DG (bid dosing, days 1–20). 2-DG at 2000 and 4000 mg/kg/day bid were toxic, with deaths observed at 18 and 9 days, respectively. The treatment was well tolerated with acceptable changes in body weight.

These studies show that the MTD of 2-DG in tumor-free nude mice is 4000 mg/kg/dose for 5 days of bid dosing. 2-DG at 2000 mg/kg/dose does not increase the toxicity of 2, 3, or 4 mg/kg cisplatin. 2-DG alone did not affect the growth rate of MV522 xenograft tumors in nude mice. A combination therapy of 2-DG and cisplatin gave significant improvements in TGD in one study, but not in a second study. These results are consistent with the combination of 2-DG and cisplatin being more effective than cisplatin alone when the cisplatin is started while the tumors are fairly small (70 mg). Paclitaxel and 2-DG showed a significant increase in TGD, compared to paclitaxel alone, at a dose where paclitaxel alone had no effect (10 mg/kg/dose, i.p., bid). In this study paclitaxel dosing did not begin until the average tumor size was 200 mg, a more challenging test of this drug combination. In general, doses of 2-DG<1500 mg/kg/dose (bid to sacrifice) or 2000 mg/kg/dose bid for only 10 days, in combination with cisplatin or paclitaxel were well-tolerated and not more toxic than the chemotherapy alone. These data support use of 2-DG/paclitaxel as a chemotherapeutic combination for treatment of cancer.

Other dose escalation studies showed that a single dose of orally administered 2-DG is non-toxic to rats at the maximum deliverable oral dose (4.5 g/kg). In dogs, this maximum dose led to emesis at 1 hour but no other visible toxicity. Single oral doses of 2 g/kg were well tolerated in dogs with no observations other than minor emesis. In multiple dose (5-day) studies of 2-DG at 1 g/kg in the rat, and 0.25 g/kg in the dog, no visible signs of toxicity have been observed. Thus, 2-DG can be administered to mammals at therapeutically effective doses with no or minimal side effects.

EXAMPLE 3

Oral Formulations of 2-DG

This example illustrates the preparation of representative pharmaceutical formulations for oral administration.

A. 2-DG is dispensed into hard-shell gelatin capsules containing between 100 mg and 1 g of 2-DG; optionally, about 0.5% (weight/weight) magnesium stearate can be added. In addition, a mixture of 2-DG and lactose can be used in the capsule.

B. 2-DG (20.0%–89.9% wt./wt., depending on whether lactose is present, and how much); magnesium stearate (0.9%); starch (8.6%); optionally lactose (0–69.6%) and PVP (polyvinylpyrrolidine; 0.9%) are, with the exception of the magnesium stearate, combined and granulated using water as a granulating liquid. The formulation is then dried, mixed with the magnesium stearate and formed into tablets with a tableting machine.

C. 2-DG is dissolved in a mixture of propylene glycol, polyethylene glycol 400, and polysorbate 80; water is added; and the resulting mixture is dispensed into bottles.

D. A mixture of 2-DG (20% to 60% wt./wt.), peanut oil (38%–78%), and 2.0% (wt./wt.) Span 60 is prepared, melted, mixed, and filled into soft elastic capsules.

E. A liquid formulation of 2-deoxy-D-glucose (100 mg/mL); Methylparaben, NF (1.8 mg/mL); and Propylparaben, NF (0.2 mg/mL) in purified water is prepared in 40 mL clear Type I glass vials (with screw cap), as follows. The nominal fill volume is 20 mL, and the target fill volume is 23 mL (in-process range: 22–24 mL). About 40% batch volume of purified water is placed in a suitable size container. The water is heated to and maintained at a temperature of 70±5° C. Accurately weighed methylparaben and propylparaben are transferred to the hot water and mixed to dissolve. After completion of dissolution, 2-DG is added and mixed to dissolve. The solution is diluted to final volume or weight (density= 1.025 g/mL) with purified water and mixed thoroughly; then, the solution is filtered through a 0.2-micron filter into a clean receiving vessel. The solution is filled into vials and the vials capped. An in-process check of appearance, pH (range 5.0–7.0), and 2-DG content by HPLC (range: 95.0–105.0 mg/mL) is performed.

EXAMPLE 4

Combination Studies

This example reports the results of testing the effects of 2-DG and other anti-cancer agents to determine if 2-DG acts synergistically under the conditions and in the two cell lines listed below. This in vitro study design reveals synergistic effects only under the conditions and in the cell line employed, so evidence of synergy cannot be extrapolated to other conditions or cell lines. For example, because the studies were carried out under normoxic conditions, these tests mimic the effects of 2-DG and the other agent(s) tested on the normoxic (and not hypoxic) regions of a tumor. Therefore, the absence of synergistic effects (i.e., additive or antagonistic) in this test system does not indicate a lack of efficacy for in vivo treatment of cancer. In addition, synergistic effects observed in one cell line do not inidcate that the same (or similar) effects would be observed in another cell lines. Certain combinations of 2-DG and another anti-cancer agent for which synergy was seen in one cell line in this test system were not synergistic in other cell lines in this test system.

A. 2-DG and 5-FU. Human tumor cell lines MiaPaCa-2 pancreatic carcinoma (mutant ras, gemcitabine sensitive) and HT-29 colon carcinoma (polyposis type, mutant p53 and APC, chemosensitive) were purchased from the ATCC (Rockville, Md.). The cell lines were cultured in RPMI-1640 medium with 11 mM glucose (Invitrogen, Carlsbad, Calif.) in 10% fetal bovine serum (Nova Tech). The cells were cultured at 37° C. in a humidified atmosphere containing 5% CO2. Cells grown to 70% confluency were trypsinized and resuspended into cell culture medium at a concentration of $10^5$ cells/ml. On Day 0 of the experiment, a 100 mL aliquot of tumor cells was plated into internal wells of a 96-well microtiter plate at an appropriate density (in the range of $2 \times 10^3$ to $10^4$ cells/well). The cells were incubated for 24 hours to allow maximum adhesion prior to exposure with test agents. Ultra pure 2-DG was purchased from Sigma-Aldrich (St. Louis, Mo.) and dissolved in water to prepare a 1 M stock solution. For the cell culture studies, 2-DG was diluted in cell culture medium and evaluated at 0 (vehicle), 0.006, 0.032, 0.16, 0.8, 4, 20, and 100 mM concentrations in cell culture medium. 5-Fluorouracil (5-FU) was purchased from Sigma-Aldrich and dissolved in 100% DMSO to prepare a 1000× stock solution. For the cell culture studies, 5-FU was diluted in cell culture medium to a final concentration of 0.1% DMSO and evaluated at 0 (vehicle, 0.1% DMSO), 0.006, 0.032, 0.16, 0.8, 4, 20, and 100 microg/mL concentrations in cell culture medium.

For the single agent studies, cultures of tumor cells were treated 6 hours after plating (Day 0) with 2-DG in eight serial dilutions starting at 100 mM. The starting concentration and the test range of 5-FU were determined empirically for each cell line. Treatment with 5-FU started on Day 1. There were 6 replicates for each dose determination. Both drugs were added once without the medium change. After 3 days in culture, the number of proliferating cells was measured by the MTS assay described below. The test was repeated twice to quantify growth inhibitory activity. The above dose range of 2-DG and 5-FU was evaluated to determine $IC_{50}$ values for growth inhibition (50% effective dose). $IC_{50}$ values were generated from two separate experiments.

For the combination studies, the cells were plated as described above on Day 0 and pre-exposed to 2-DG after 6 hours. The treatment with 5-FU began on Day 1. 2-DG and 5-FU were tested at their respective $IC_{50}$ concentrations as determined from the single agent studies with the drugs combined in different proportions. The combination studies were used to characterized the type of drug-drug interaction (additive, synergistic, or antagonistic).

The MTS assay was used to evaluate the growth inhibitory activity of 2-DG and 5-FU. The MTS reagent is a tetrazolium compound and an electron coupling reagent. The MTS tetrazolium compound is bioreduced by cells into a colored formazan product soluble in cell culture medium. The conversion is catalyzed by NADPH or NADH produced by dehydrogenase enzymes in metabolically active cells. The MTS assay is a colorimetic assay based upon the ability of viable cells to convert MT to formazan; the quantity of formazan product, as measured by the 490 nm absorbance, is directly proportional to the number of viable cells in culture. An automated procedure determines the $IC_{50}$ value. Exponentially growing cells in 100 mL of cell culture medium are plated on Day 0 in 96-well microtiter plates at a concentration of $10^4$ cells/well. On Day 1, drugs are added to each well of the microtiter plate with the designated concentration in 100 mL aliquots of cell culture medium plus vehicle and incubated at 37° C. in a humidified incubator (5% CO2/95% HEPA filtered air) for designated time periods. At the end of the designated time period, 100 microL of growth medium is removed. The cells are then incubated with 20 microL of MTS tetrazolium compound (1.9 mg/mL in PBS, pH 6.0, 3-(4,5-dimethylthiazol-2-yl)-5-(3-carboxymethoxyphenyl)-2-(4-sulfophenyl)-2-tetrazolium, inner salt) for one hour at 37° C. Absorbance is documented on a Dynex HD microplate reader at a wavelength of 490 nm.

The data was calculated as percent growth inhibition, wherein 0% represents the mean value in wells to which only vehicle (cell culture medium) was added. The % Growth Inhibition was calculated as follows: % Growth Inhibition=$(1-(OD_{test}/OD_{vehicle}) \times 100$, where $OD_{test}$ is the optical density of the tested sample, and $OD_{vehicle}$ is the optical density of the vehicle in which each respective drug is dissolved. An $IC_{50}$ value was determined from % Growth Inhibition values using PRISM GraphPad software and the formula described in Example 2. For the combination studies, statistical comparisons were made with each test combination, and the endpoints (100:0 2-DG and 0:100 5-FU). To determine the interaction, there must be a significant difference that exists between the combination absorbance values and both endpoint values. For example, if the values are statistically ($p<0.05$) above or below the absorbance values of either agent tested alone, then antagonism or synergy is described. Otherwise, the interaction is considered more consistent with an additive interaction.

The results of the single agent studies showed that the mean $IC_{50}$ for the colon tumor cell line HT-29 was 9.83 mM for 2-DG and 1.90 microg/mL for 5-FU. The pancreatic tumor cell line MiaPaCa-2 produced $IC_{50}$ values of 2.62 mM for 2-DG and 2.58 microg/mL with 5-FU. The results of the combination studies showed that the two compounds interacted in an additive to synergistic manner, with strong indications of synergism at higher ratios of 5-FU:2-DG (>60:40).

B. Other Anti-Neoplastic Agents. Synergism studies were conducted with H460 cells and 2-DG (at concentrations of either 1 mM or 10 mM) in combination with other anti-neoplastic agents, including the following: 1 mM 2-DG and 0.37 and 1.1 microM Adriamycin; 10 mM 2-DG and 0.12, 0.37, and 1.1 microM Adriamycin; 10 mM 2-DG and 1.2, 3.7, and 11 microM Etoposide; 1 mM 2-DG and 0.012, 0.037, 0.11, and 0.33 microM Carboplatin; 10 mM 2-DG and 0.0013, 0.004, 0.012, 0.037, 0.11, and 0.33 microM Carboplatin; 1 mM 2-DG and 0.4, 1.2, 3.7, 11, and 33 microM Cisplatin; 10 mM 2-DG and 0.14, 0.4, 1.2, 3.7, 11, and 33 microM Cisplatin; and 1 and 10 mM 2-DG and 0.0012, 0.004, 0.012, 0.037, 0.11, and 0.33 microM Taxol.

EXAMPLE 5

2-DG Sensitizes a Taxane-Resistant Tumor Cell Line to Taxol

Taxol™ (Bristol-Myers Squibb; paclitaxel) inhibits the proliferation of most human non-small cell lung cancer (NSCLC) tumor cell lines with an $IC_{50}$ ranging from 50–200 nM. Such cell lines include H460, H23, H522 and H661 cells. However, H2347 cells are resistant to treatment with Taxo™, which against these cells has an $IC_{50}$ greater than 1 μM. When simultaneously treated with 1 mM 2-DG (a concentration which has no effect on proliferation by itself) and Taxol, each of these cell lines (including the Taxol™ resistant line) show increased sensitivity to Taxo™. For example, in one test, 200 nM Taxol™ inhibited proliferation by ~20%, while treatment of cells with both 2-DG (1 mM) and Taxol™ resulted in a 50% inhibition of proliferation. Thus, 2-DG can be used to sensitize cancer cells and tumors to drugs to which those cells and tumors are resistant in the absence of 2-DG.

EXAMPLE 6

2-DG/Paclitaxel Dosing Study

The mouse MV522 xenograft model substantially as described in Example 2 was used to compare the effects of dosing 2-DG orally (in water) either at a single dose of 4 g/kg or in multiple doses (twice a day at 2 g/kg) in various combinations with paclitaxel dosed i.p. as a single dose (30 mg/kg) or in multiple doses (once daily at 10 mg/kg). The dose regimens employed are shown in Table II below, and the results are plotted in the graphs shown in FIG. 1.

TABLE II

Dose Regimen for 2-DG (2) and Paclitaxel (P) in Dose Sequence Study

| Group | \multicolumn{15}{c}{Day of Treatment} |
|---|---|---|---|---|---|---|---|---|---|---|---|---|---|---|---|

| Group | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 4(6), 0* |   |   |   |   |   | 2 |   |   |   |   |   |   |   |   |   |
| 0, 30(6) |   |   |   |   |   | P |   |   |   |   |   |   |   |   |   |
| 4(5), 30(6) |   |   |   |   | 2 | P |   |   |   |   |   |   |   |   |   |
| 4(6), 30(6) |   |   |   |   |   | P 2 |   |   |   |   |   |   |   |   |   |
| 4(7), 30(6) |   |   |   |   |   | P | 2 |   |   |   |   |   |   |   |   |
| 2(1–5), 0 | 2 | 2 | 2 | 2 | 2 |   |   |   |   |   |   |   |   |   |   |
| 2(6–10), 0 |   |   |   |   |   | 2 | 2 | 2 | 2 | 2 |   |   |   |   |   |
| 2(11–15), 0 |   |   |   |   |   |   |   |   |   |   | 2 | 2 | 2 | 2 | 2 |
| 2(1–10), 0 | 2 | 2 | 2 | 2 | 2 | 2 | 2 | 2 | 2 | 2 |   |   |   |   |   |
| 0, 10(6–10) |   |   |   |   |   | P | P | P | P | P |   |   |   |   |   |
| 2(1–5), 10(6–10) | 2 | 2 | 2 | 2 | 2 | P | P | P | P | P |   |   |   |   |   |

TABLE II-continued

Dose Regimen for 2-DG (2) and Paclitaxel (P) in Dose Sequence Study

| Group | Day of Treatment | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 2(6–10), 10(6–10) | | | | | | P2 | P2 | P2 | P2 | P2 | | | | | |
| 2(11–15), 10(6–10) | | | | | | P | P | P | P | P | 2 | 2 | 2 | 2 | 2 |
| 2(1–10), 10(6–10) | 2 | 2 | 2 | 2 | 2 | P2 | P2 | P2 | P2 | P2 | | | | | |

*2-DG dose in g/kg (day of dosing), paclitaxel dose in mg/kg (day of dosing)

The results showed that administration of 2-DG alone results in a small delay in tumor growth, with 10 days of dosing being more effective than 5 in this model. The results also showed that a single dose of paclitaxel at 30 mg/kg is more effective than 5 doses of paclitaxel at 10 mg/kg. A single dose of 2-DG did not increase the efficacy of a single dose of paclitaxel. In combination with 5 days of paclitaxel treatment, 5 days of 2-DG dosing resulted in a small increase in tumor growth delay (TGD), whereas 10 days of 2-DG dosing resulted in a significant ($p<0.05$) increase in TGD. The effect of 2-DG and paclitaxel in combination on TGD appears to be additive. In this model, dosing 2-DG with, or after, paclitaxel gave better efficacy than dosing 2-DG before paclitaxel. For treatment of humans, generally 6–10 dosing of paclitaxel is not used; instead paclitaxel may be administered once weekly, for example. Dosing 2-DG days 1–10 (as in model) with once weekly paclitaxel is essentially continuous dosing of 2-DG. This suggests that, for every three week dosing of paclitaxel, intermittent or continuous dosing of 2-DG could be used. Once-a-day or lower doses of 2-DG may be equally efficacious.

EXAMPLE 7

Treatment of Cancer with Docetaxel and 2-DG

The following prophetic example is provided to illustrate treatment of cancer with 2-DG combination therapy. 2-DG is administered to male and female cancer patients, at least 18 years of age, who have histologically confirmed, locally advanced, or metastatic solid malignancy (originating from lung cancer, head/neck cancer, breast cancer, esophageal cancer, gastric cancer, pancreatic cancer, prostate cancer or biliary tract cancer) and were previously treated with at least one chemotherapy regimen for advanced or metastatic disease or no curative standard treatment is available for the patient's cancer. The 2-DG is administered after fasting overnight and at least one hour before breakfast. The 2-DG is supplied in a 40-mL clear glass screw cap vial containing 20 mL nominal (23 mL target fill) of a solution of 2-DG formulated at a concentration of 100 mg/mL, methylparaben at 1.8 mg/mL, propylparaben at 0.2 mg/mL in water for injection.

The 2-DG is administered orally. The 2-DG can be diluted (if desired) to a volume of 100 mL in bacteriostatic water for injection and then administered orally, following, as noted, an overnight fast (water allowed). If doses above 100 mg/kg are employed and a very large (>100 mg/kg) patient is treated, undiluted 2-DG at the indicated concentration is employed. However, dosing will typically be targeting levels equal to or higher than 2 mg 2-DG per kg of patient weight, typically in the range of 25 to 100 mg/kg, and often in the range of 25 to 50 mg of 2-DG per kg of patient weight. Each oral dose of 2-DG is administered 1 hour before breakfast. Each dose of 2-DG is followed by administration of one rinse of the dosing container of approximately 50 mL of water. Patients are allowed to add Crystal Light to their 100 mL oral dose solution, if preferred, for palatability.

In a first embodiment, 2-DG is co-administered with docetaxel, with 2-DG administered orally on Days 1–7 and Days 15–21, and docetaxel administered by IV infusion once a week during Weeks 24 and 6–8. This dosing schema is shown in Table III.

TABLE III

| | Week 1 | Week 2 | Week 3 | Weeks 4, 6, 7, 8 |
|---|---|---|---|---|
| 2-DG | X | 0 | X | 0 |
| Docetaxel (30 mg/m$^2$) | 0 | X | X | X |

An alternative dosing schema is shown in Table IV. This schema may continue for 3 cycles of 8 weeks if the physician believes such continued treatment to be useful.

TABLE IV

| | Weeks 1/5 | Weeks 2/6 | Weeks 3/7 | Weeks 4/8 |
|---|---|---|---|---|
| 2-DG | X | 0 | X | 0 |
| Docetaxel (30 mg/m$^2$) | 0 | X | X | X |

In one embodiment, dosing of 2-DG is continued beyond the 6 months contemplated by the above schedule. As noted, 2-DG can also be continuously administered during the entire dosing regimen for docetaxel (the approved docetaxel dosing regimen is every 3 weeks).

EXAMPLE 8

Treatment of Prostate Cancer with 2-DG

The following prophetic example is provided to illustrate treatment of prostate cancer with 2-DG therapy. Male subjects from 40 through 70 years of age with untreated prostate cancer are treated in accordance with the methods of the invention by administration of 50 mg of 2-DG per kg of patient weight. Each oral dose of 2-DG is administered following an overnight fast. The prostate is then examined by magnetic resonance imaging, such as MRSI, or otherwise to determine if there have been substantive metabolic changes (decreased production of ATP and/or citrate). Depending on the metabolic changes observed, the dose may be reduced (where the change is deemed to be in excess of that required) to, for example and without limitation, 15 mg/kg, or increased (where no metabolic change is observed) to, for example and without limitation, 70 mg/kg).

EXAMPLE 9

2-DG Analogs

Figure 2:
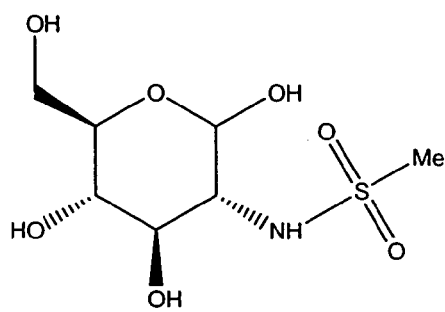
FIG. 2 shows the structures of certain 2-DG analogs.
Figure 2:
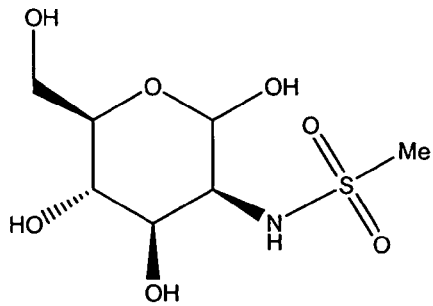
Figure 2:
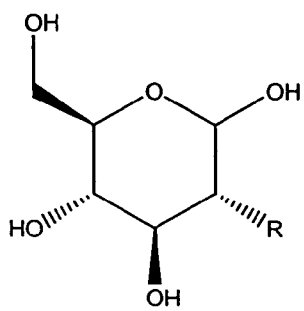
Figure 2:
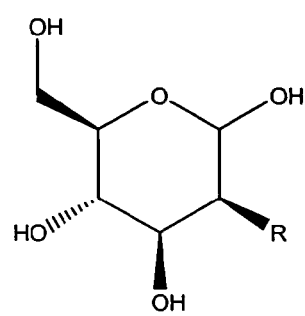
Figure 2:
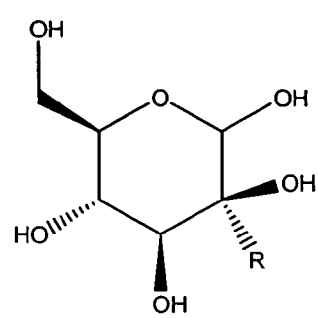
Figure 2:
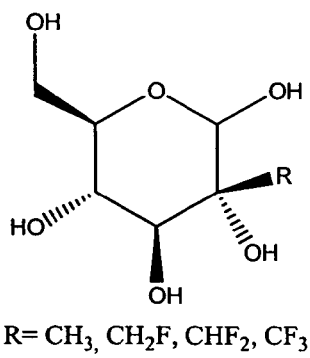
Figure 2:
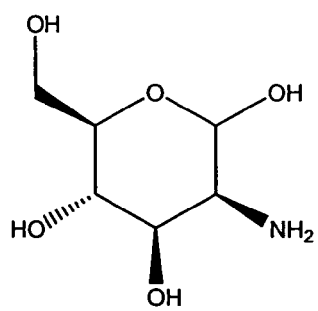
Figure 2:
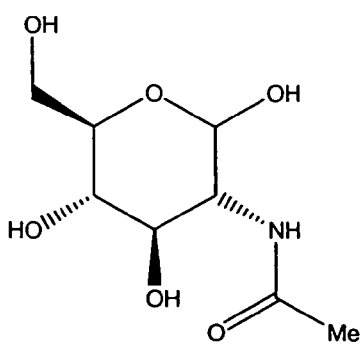
Figure 2:
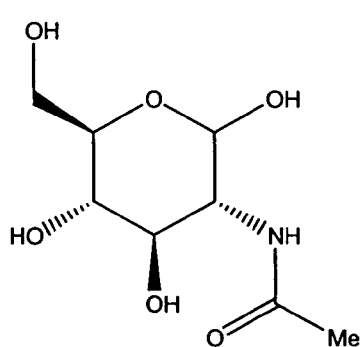

In a different embodiment of the invention, certain 2-DG analogs can be used in place of 2-DG in the methods and compositions of the invention. As used herein, a 2-DG analog is any D-glucose analog other than 2-DG that does not have a hydroxyl group at the 2 position of the glucose ring. L-glucose and its L-analogs are not 2-DG analogs for purposes of the present invention. A glucose analog includes mannose, galactose, gulose, and 5-thio-glucose. An analog of glucose or 2-DG can have a fluorine in place of a hydrogen at any position on the glucose ring; thus, 2-fluoro-2-deoxy-D-glucose (2-FDG) and 2-difluoro-2-deoxy-D-glucose are 2-DG analogs. An analog of glucose or 2-DG can have anamino group in place of a hydroxyl group at any position on the glucose ring other than the 6 position; thus, 2-amino-2-deoxy-D-glucose (2-glucosamine) and 2-amino-2-deoxy-D-galactose (2-galactosamine) are 2-DG analogs. Other illustrative 2-DG analogs include 2-F-mannose, 2-mannosamine, 2-deoxygalactose, 2-F-deoxygalactose, and di, tri, and other oligosaccharades that contain one or more of the preceding or following 2-DG analogs. Other 2-DG analogs useful in the methods of the present invention include the analogs shown in FIG. 2. Analogs useful for treatment of cancer and other diseases are commercially available and/or can be synthesized by one of skill using routine techniques with reference to the scientific literature.

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, to achieve the benefits provided by the present invention without departing from the scope of the present invention. All such modifications are intended to be within the scope of the claims appended hereto. All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

What is claimed is:

1. A method of treating cancer in a human cancer patient, which method comprises administering to said patient a therapeutically effective dose of 2-deoxy-D-glucose (2-DG), said therapeutically effective dose obtained by orally administering 2-DG daily to said patient in a range of about 25 mg of 2-DG per kg of patient weight to about 150 mg of 2-DG per kg of patient weight for at least five consecutive days.

2. The method of claim 1 wherein said 2-DG is administered daily for at least two weeks.

3. The method of claim 1, wherein said 2-DG is administered daily for at least one week.

4. The method of claim 1, wherein said 2-DG is administered daily for at least ten consecutive days.

5. The method of claim 1, wherein said daily dose is in the range of about 1 mg of 2-DG per kg of patient weight to about 1 g/kg.

6. The method of claim 1, wherein said daily dose is in the range of about 25 mg/kg to about 50 mg/kg.

7. A method of treating a human cancer patient, which method comprises administering to said patient a therapeutically effective dose of 2-DG in combination with another anti-cancer agent, wherein the therapeutically effective dose of 2-DG is obtained by orally administering 2-DG daily in a range of about 25 mg of 2-DG per kg of patient weight to about 150 mg of 2-DG per kg of patient weight for at least five consecutive days.

8. The method of claim 7, wherein said cancer is a multi-drug resistant cancer.

9. The method of claim 8, wherein said anti-cancer agent is an agent to which said cancer is resistant in the absence of 2-DG.

10. The method of claim 7, wherein said anti-cancer agent is administered to the mammal at a dose that is lower than the recommended effective dose for administration when not administered in combination with 2-DG.

11. The method of claim 7, wherein said cancer is a cancer selected from the group consisting of non-small-cell lung cancer, head and neck cancer, colorectal cancer, and breast cancer.

12. The method of claim 7, wherein said therapeutically effective dose of 2-DG is obtained by administering 2-DG daily for at least a week.

13. The method of claim 7, wherein said anti-cancer agent is selected from the group consisting of docetaxel, paclitaxel, cisplatin, and carboplatin.

14. A method of treating cancer in a human patient having a solid tumor, which method comprises administering to said patient a therapeutically effective dose of 2-deoxy-D-glucose (2-DG), said therapeutically effective dose obtained by orally administering 2-DG daily in a range of about 25 mg of 2-DG per kg of patient weight to about 150 mg of 2-DG per kg of patient weight for at least five consecutive days.

15. A method of treating cancer in a human cancer patient, which method comprises co-administering to said patient (i) a therapeutically effective dose of 2-deoxy-D-glucose (2-DG), said therapeutically effective dose obtained by orally administering 2-DG daily in a range of about 25 mg of 2-DG per kg of patient weight to about 150 mg of 2-DG per kg of patient weight for at least five consecutive days, and (ii) an anti-cancer agent selected from the group consisting of docetaxel, paclitaxel, cisplatin, and carboplatin.

16. The method of claim 15, wherein said patient has a solid tumor cancer.

17. The method of claim 1, wherein said patient has a solid tumor cancer.

* * * * *